(12) United States Patent
McEver et al.

(10) Patent No.: US 8,377,440 B2
(45) Date of Patent: Feb. 19, 2013

(54) ANTI-P-SELECTIN ANTIBODIES AND METHODS OF USING THE SAME TO TREAT INFLAMMATORY DISEASES

(75) Inventors: Rodger P. McEver, Oklahoma City, OK (US); Richard Alvarez, Edmond, OK (US); Ziad Kawar, Oklahoma City, OK (US)

(73) Assignees: Selexys Pharmaceuticals Corporation, Oklahoma City, OK (US); Oklahoma Medical Research Foundation, Oklahoma City, OK (US)

( * ) Notice: Subject to any disclaimer, the term of this patent is extended or adjusted under 35 U.S.C. 154(b) by 150 days.

(21) Appl. No.: 12/516,987
(22) PCT Filed: Nov. 30, 2007
(86) PCT No.: PCT/US2007/024692
§ 371 (c)(1), (2), (4) Date: Mar. 2, 2010
(87) PCT Pub. No.: WO2008/069999
PCT Pub. Date: Jun. 12, 2008

(65) Prior Publication Data
US 2011/0243926 A1 Oct. 6, 2011

Related U.S. Application Data
(60) Provisional application No. 60/872,170, filed on Dec. 1, 2006.

(51) Int. Cl.
A61K 39/395 (2006.01)
C07K 16/00 (2006.01)
(52) U.S. Cl. ............... 424/133.1; 830/387.1; 830/388.7; 424/173.1
(58) Field of Classification Search .................. None
See application file for complete search history.

(56) References Cited

U.S. PATENT DOCUMENTS

| | | | |
|---|---|---|---|
| 4,783,399 A | 11/1988 | Oldstone et al. | |
| 5,530,101 A * | 6/1996 | Queen et al. | 530/387.3 |
| 5,593,882 A | 1/1997 | Erbe et al. | |
| 5,800,815 A | 9/1998 | Chestnut et al. | |
| 5,859,205 A * | 1/1999 | Adair et al. | 530/387.3 |
| 6,033,667 A | 3/2000 | Chesnut et al. | |
| 6,210,670 B1 | 4/2001 | Berg | |
| 6,407,213 B1 | 6/2002 | Carter et al. | |
| 6,667,036 B2 | 12/2003 | Cummings et al. | |
| 7,223,845 B2 | 5/2007 | Cummings et al. | |
| 7,317,091 B2 | 1/2008 | Lazar et al. | |
| 7,563,441 B2 | 7/2009 | Graus et al. | |
| 7,754,867 B2 | 7/2010 | Graus et al. | |
| 2003/0198639 A1 | 10/2003 | Frenette et al. | |
| 2005/0048133 A1 | 3/2005 | Pinsky et al. | |
| 2005/0112124 A1 | 5/2005 | Frenette et al. | |
| 2006/0024298 A1 | 2/2006 | Lazar et al. | |
| 2009/0285812 A1 | 11/2009 | Alvarez et al. | |
| 2010/0209423 A1 | 8/2010 | Graus et al. | |
| 2011/0212096 A1* | 9/2011 | Rollins et al. | 424/139.1 |
| 2011/0287017 A1 | 11/2011 | Rollins et al. | |
| 2011/0293617 A1 | 12/2011 | Rollins et al. | |

FOREIGN PATENT DOCUMENTS

| | | |
|---|---|---|
| EP | 07867601.2 | 8/2010 |
| WO | WO 93/06863 | 4/1993 |
| WO | WO 93/21956 A1 | 11/1993 |
| WO | WO 94/25067 | 11/1994 |
| WO | WO 95/33484 A1 | 12/1995 |
| WO | WO 95/34324 A1 | 12/1995 |
| WO | WO 97/48485 | 12/1997 |
| WO | WO 2004/056312 A2 | 7/2004 |
| WO | WO 2005/100402 A1 | 10/2005 |
| WO | PCT/US2011/66470 | 4/2012 |

OTHER PUBLICATIONS

Vajdos et al. Comprehensive functional maps of the antigen-binding site of an anti-ErbB2 antibody obtained with shotgun scanning mutagenesis. J. Mol. Biol. Jul 5, 2000, 320(2):415-28.*
Brown et al. Tolerance of single, but not multiple, amino acid replacements in antibody VH CDR 2: a means of minimizing B cell wastage from somatic hypermutation? J. Immuno. May 1996, 3285-91.*
Rudikoff et al Single amino acid substitution altering antigen-binding specificity. Proc Natl Acad Sci U S A. Mar. 1982;79(6):1979-83.*
Paul, Fundamental Immunology, 3rd Edition, 1993, pp. 292-295.*
Beiboer et al.,Guided selection of a pan carcinoma specific antibody reveals similar binding characteristics yet structural divergence between the original murine antibody and its human equivalent. J. Mol., Biol. (2000) 296:833-849.*
Eduardo Padlan, Anatomy of the antibody molecule. Mol I mmunol. Feb. 1994 ;31 (3): 169-217.*
Klimka et al., British Journal of Cancer (2000) 83:252-260.*
MacCallum et al. J. Mol. Biol., 262, 732-745, 1996.*
Casset et al (Biochemical and Biophysical Research Communications, 307:198-205, 2003.*
International Preliminary Report on Patentability for PCT/US2007/024692, issued Jun. 3, 2009.
International Search Report for PCT/US2007/024692, mailed Oct. 7, 2008.
EP 07867601.2, McEver et al., European Examination, dated Apr. 21, 2011.

(Continued)

Primary Examiner — Maher Haddad
(74) Attorney, Agent, or Firm — Wilmer Cutler Pickering Hale and Dorr LLP

(57) ABSTRACT

The invention features antibodies, e.g., chimeric and humanized antibodies, that recognize (i.e., bind) P-selectin. The P-selectin antibodies prevent P-selectin from binding to its cognate receptor. The P-selectin antibodies can be used to treat inflammatory and thrombotic conditions, e.g., sickle cell disease, pain crisis associated with sickle cell disease, deep vein thrombosis, asthma, rheumatoid arthritis, psoriasis, and ischemia reperfusion injury in a patient in need thereof.

7 Claims, 5 Drawing Sheets

OTHER PUBLICATIONS

EP 07867601.2, McEver et al., Response to European Examination of Apr. 21, 2011, filed Oct. 20, 2011.

Geng et al., "Neutrophil in Recognition Requires a $Ca^{2+}$-induced Conformational Change in the Lectin Domain of GMP-140*", The Journal of Biological Chemistry, vol. 266, pp. 22313-22318 (1991).

Berg EL, Fromm C, Melrose J, Tsurushita N. Antibodies cross-reactive with E- and P-selectin block both E- and P-selectin functions. Blood, Jan. 1, 1995.;85(1):31-7. PMID: 7528571.

Mehta P, Patel KD, Laue TM, Erickson HP, Mcever RP. Souluble monomeric P-selectin containing only the lectin and epidermal growth factor domains binds to P-selectin glycoprotein ligand-1 on leukocytes. Blood, Sep. 15, 1997.; 90(6): 2381-9. PMID: 9310489.

Ruchaud-Sparangano MH, Malaud E, Gayet O, Chignier E, Buckland R, McGregor JL. Mapping the epitope of a functional P-selectin monoclonal antibody (LYP20) to a short complement-like repeat (SCR 4) domain: use of human-mouse chimera and homologue-replacement mutagenesis. Biochem. J., 1998. 1;332(Pt2):309-14. PMID: 9601057.

Hirose M, Kawashima H, Miyasaka M. A functional epitope on P-selectin that supports binding of P-selectin to P-selectin glycoprotein ligand-1 but not to sialyl Lewis X oligosaccharides. Int. Immunol., May 1998.; 10(5): 639-49. PMID: 9645612.

Leppanen A, Mehta P, Ouyang YB, Ju T, Helin J, Moore KL, van Die I, Canfield WM, McEver RP, Cummings RD. 1999. A novel glycosulfopeptide binds to P-selectin and inhibits leukocyte adhesion to P-selectin. J Biol Chem Aug. 27;274(35):24838-48. PMID: 10455156.

Kaul, et al., "Hypoxia/reoxygenation causes inflammatory response in transgenic sickle mice but not in normal mice," *Journal of Clinical Investigation, American Society for Clinical Investigation*, (Aug. 1, 2000) pp. 411-420, vol. 106, No. 3.

Matsui NM, Borsig L, Rosen SD, Yaghmai M, Varki A, Embury SH P-Selecin Mediates the adhesion of sickle erythrocytes to the endothelium. Blood, 2001. 98(6): p. 1955-62. PMID: 11535535.

Somers WS, Tang 3, Shaw GD, Camphausen RT. Insights into the molecular basis of leukocyte tethering and rolling revealed by structures of P- and E-selectin bound to SLe(X) and PSGL-1. Cell, Oct. 27, 2000.;103(3):467-79. Erratum in: Cell, Jun. 29, 2001.;105(7):971. PMID: 11081633.

Turhan A, Weiss LA, Mohandas N, Collier BS, Freette PS. Primary role for adherent leukocytes in sickle cell vascular occlusion: a new paradigm. Proc Natl Acad Sci U S A, 2002. 99(5): p. 3047-51. PMID: 1180644.

Hebbel RP, Osarogiagbon R, and Kaul D. The endothelial biology of sickle cell disease: inflammation and a chronic vasculopathy. Microcirculation, 2004. 11(2): p. 129-51. Review. PMID: 15280088.

Chiang EY and Frenette PS. Sickle cell vaso-occlusion. Hematol Oncol Clin North Am, 2005. 19(5): p. 771-84, Review. PMID: 16214643.

Embury, et al., "The contribution of endothelial cell P-selectin to the microvascular flow of mouse sickle erythrocytes in vivo," *Blood, American Society of Hematology*, (Nov. 15, 2004) pp. 3378-3385, vol. 104, No. 10.

Okpala I, Leukocyte adhesion and the pathophysiology of sickle cell disease. Curr Opin Hematol, 2006. 13(1): p. 40-4. Review. PMID: 16319686.

Embury, SH. The not-so-simple process of sickle cell vasoocclusion. Microcirculation, 2004. 11(2): p. 101-13. PMID: 15280086.

Moore et al., "P-selectin glycoprotein ligand-1 mediates rolling of human neutrophils on P-selectin" *J. Cell Biol.* (Feb. 1995) vol. 128(4): pp. 661-671.

Ramachandran et al., "Tyrosine replacement in P-selectin glycoprotein ligand-1 affects distinct kinetic and mechanical properties of bonds with P- and L-selectin" *PNAS* (Nov. 23, 1999) vol. 96, No. 24, pp. 13771-13776.

Ushiyama et al., "Structural and Functional Characterization of Monomeric Soluble P-selectin and Comparison with Membrane P-selectin" *The Journal of Biological Chemistry* (Jul. 15, 1993) vol. 268, No. 20, pp. 15229-15237.

Xu et al., "Diversity in the CDR3 region of VH is sufficient for most antibody specificities" *Immunity* (Jul. 2000) vol. 13, pp. 37-45.

Zimmerman et al., "Thrombin Stimulates the Adherence of Neutrophils to Human Endothelial Cells in Vitro" *J. Clin. Invest.* (Dec. 1985) vol. 76, pp. 2235-2246.

EP 07867601.2, McEver et al., European Office Action dated Jan. 24, 2012.

EP 07867601.2, McEver et al., Response to European Office Action of Jan. 24, 2011, filed Feb. 15, 2012.

U.S. Appl. No. 12/974,739, Rollins et al., Preliminary Amendment, filed Aug. 9, 2011.

U.S. Appl. No. 12/974,739, Rollins et al., Second Preliminary Amendment, filed Jan. 10, 2012.

U.S. Appl. No. 13/204,508, Rollins et al., Office Action Restriction, dated Oct. 21, 2011.

U.S. Appl. No. 13/204,508, Rollins et al., Amendment and Response, mailed Jan. 4, 2012.

U.S. Appl. No. 13/204,508, Rollins et al., Office Action, dated Feb. 21, 2012.

\* cited by examiner

```
G1-VK        DIVLTQSPASLAVSLGQRATISCKASQSVDYDGHSYMNWYQQKPGQPPKLLIYAASNLESGIPARFSGSGSGTDFTLNIHPVEEEDAATYYCQQSDENPLTFGTGTKLELK   SEQ ID NO: 44
AAZ0906      DIQMTQSPSSLSASVGDRVTITCRASQSI SS....YLNWYQQKPGKAPKLLIYAASSLQSGVPSRFSGSGSGTDFTLTISSLQPEDFATYYCQQSYSTPLTFGGGTKVEIK    SEQ ID NO: 45
Hu-G1-VK_v1  DIQMTQSPSSLSASVGDRVTITCKASQSVDYDGHSYMNWYQQKPGKAPKLLIYAASNLESGVPSRFSGSGSGTDFTLTISSLQPEDFATYYCQQSDENPLTFGGGTKVEIK    SEQ ID NO: 46
Hu-G1-VK_v2  DIQLTQSPSSLSASVGDRVTITCKASQSVDYDGHSYMNWYQQKPGKAPKLLIYAASNLESGIPSRFSGSGSGTDFTLTISSLQPEDFATYYCQQSDENPLTFGGGTKVEIK    SEQ ID NO: 47
```

VL:    Chimeric vs human sequence: 66.7%
       Humanized vs human sequence: 87.4% (v1) and 85.6 % (v2)

```
G1-VH      QVQLQQSGPELVKPGALVKISCKASGYTFTSYDINWVKQRPGQGLEWIGWIYPGDGSIKYNEKFKGKATLTVDKSSSTAYMQVSSLTSENSAVYFCARRGEYGNYEGAMDYWGQGTTVTVSS       SEQ ID NO: 48
AAC18323   QVQLVQSGAEVKKPGASVKVSCKVSGYTLTELSMHWVRQAPGKGLEWMGGFDPEDGETIYAQKFQGRVTMTEDTSTDTAYMELSSLRSEDTAVYYCATPVGRGSSTSCADYWGQGTLVTVSS       SEQ ID NO: 49
Hu-G1-VH_v1 QVQLVQSGAEVKKPGASVKVSCKVSGYTFTSYDINWVRQAPGKGLEWMGWIYPGDGSIKYNEKFKGRVTMTVDKSTDTAYMELSSLRSEDTAVYYCARRGEYGNYEGAMDYWGQGTLVTVSS      SEQ ID NO: 50
Hu-G1-VH_v2 QVQLVQSGAEVKKPGASVKVSCKVSGYTFTSYDINWVRQAPGKGLEWIGWIYPGDGSIKYNEKFKGKATLTVDKSTDTAYMELSSLRSEDTAVYYCARRGEYGNYEGAMDYWGQGTLVTVSS      SEQ ID NO: 51
```

VH:   Chimeric vs human sequence: 62.2%
      Humanized vs human sequence: 82.9 % (v1) and 79.3% (v2)

SEQUENCE LISTING

```
<160> NUMBER OF SEQ ID NOS: 59

<210> SEQ ID NO 1
<211> LENGTH: 15
<212> TYPE: PRT
<213> ORGANISM: Artificial Sequence
<220> FEATURE:
<223> OTHER INFORMATION: Synthetic

<400> SEQUENCE: 1

Lys Ala Ser Gln Ser Val Asp Tyr Asp Gly His Ser Tyr Met Asn
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Ala Ala Ser Asn Leu Glu Ser
1               5
```

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Gln Gln Ser Asp Glu Asn Pro Leu Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic

<400> SEQUENCE: 4

Ser Tyr Asp Ile Asn
1               5

<210> SEQ ID NO 5
<211> LENGTH: 17
<212> TYPE: PRT
<213> ORGANISM: Artificial Sequence
<220> FEATURE:
<223> OTHER INFORMATION: Synthetic

<400> SEQUENCE: 5

Trp Ile Tyr Pro Gly Asp Gly Ser Ile Lys Tyr Asn Glu Lys Phe Lys
1               5                   10                  15

Gly

<210> SEQ ID NO 6
<211> LENGTH: 13
<212> TYPE: PRT
<213> ORGANISM: Artificial Sequence
<220> FEATURE:
<223> OTHER INFORMATION: Synthetic

<400> SEQUENCE: 6

Arg Gly Glu Tyr Gly Asn Tyr Glu Gly Ala Met Asp Tyr
1               5                   10

<210> SEQ ID NO 7
<211> LENGTH: 336
<212> TYPE: DNA
<213> ORGANISM: Artificial Sequence
<220> FEATURE:
<223> OTHER INFORMATION: Synthetic

<400> SEQUENCE: 7
gacattgtgc taacccaatc tccagcttct ttggctgtgt ctctagggca gagggccacc      60
atctcctgca aggccagcca agtgttgat tatgatggtc atagttatat gaactggtac     120
caacagaaac caggacagcc acccaaactc ctcatctatg ctgcatccaa tctagaatct     180
gggatcccag ccaggtttag tggcagtggg tctgggacag acttcaccct caacatccat     240
cctgtggagg aggaggatgc tgcaacctat tactgtcagc aaagtgatga aaatccctc      300 acgttcggta ctgggaccaa gctggagctg aaacgg                               336

<210> SEQ ID NO 8
<211> LENGTH: 112
<212> TYPE: PRT

```
<213> ORGANISM: Artificial Sequence
<220> FEATURE:
<223> OTHER INFORMATION: Synthetic

<400> SEQUENCE: 8

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly His Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asp
                85                  90                  95

Glu Asn Pro Leu Thr Phe Gly Thr Gly Thr Lys Leu Glu Leu Lys Arg
            100                 105                 110

<210> SEQ ID NO 9
<211> LENGTH: 336
<212> TYPE: DNA
<213> ORGANISM: Artificial Sequence
<220> FEATURE:
<223> OTHER INFORMATION: Synthetic

<400> SEQUENCE: 9
gacattgtgc tgacccaatc tccagcttct ttggctgtgt ctctagggca gagggccacc    60
atctcctgca aggccagcca aagtgttgat tatgatggtc atagttatat gaactggtac   120
caacagaaac aggacagcc acccaaactc ctcatctatg ctgcatccaa tctagaatct   180
gggatcccag ccaggtttag tggcagtggg tctgggacag acttcaccct caacatccat   240
cctgtggagg aggaggatgc tgcaacctat tactgtcagc aaagtgatga aaatccctc   300 acgttcggta ctgggaccaa gctggagctg aaacgg                             336

<210> SEQ ID NO 10
<211> LENGTH: 112
<212> TYPE: PRT
<213> ORGANISM: Artificial Sequence
<220> FEATURE:
<223> OTHER INFORMATION: Synthetic

<400> SEQUENCE: 10

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly His Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asp
                85                  90                  95

Glu Asn Pro Leu Thr Phe Gly Thr Gly Thr Lys Leu Glu Leu Lys Arg
            100                 105                 110
```

<210> SEQ ID NO 11
<211> LENGTH: 336
<212> TYPE: DNA
<213> ORGANISM: Artificial Sequence
<220> FEATURE:
<223> OTHER INFORMATION: Synthetic

<400> SEQUENCE: 11

```
gacatccaga tgacacagtc tccagcttct ttggctgtgt ctctagggca gagggccacc    60
atctcctgca aggccagcca agtgttgat tatgatggtc atagttatat gaactggtac   120
caacagaaac caggacagcc acccaaactc ctcatctatg ctgcatccaa tctagaatct   180
gggatcccag ccaggtttag tggcagtggg tctgggacag acttcaccct caacatccat   240
cctgtggagg aggaggatgc tgcaacctat tactgtcagc aaagtgatga aaatcccctc   300
acgttcggta ctgggaccaa gctggagctg aaacgg                             336
```

<210> SEQ ID NO 12
<211> LENGTH: 112
<212> TYPE: PRT
<213> ORGANISM: Artificial Sequence
<220> FEATURE:
<223> OTHER INFORMATION: Synthetic

<400> SEQUENCE: 12

```
Asp Ile Gln Met Thr Gln Ser Pro Ala Ser Leu Ala Val Ser Leu Gly
1               5                   10                  15
Gln Arg Ala Thr Ile Ser Cys Lys Ala Ser Gln Ser Val Asp Tyr Asp
            20                  25                  30
Gly His Ser Tyr Met Asn Trp Tyr Gln Gln Lys Pro Gly Gln Pro Pro
        35                  40                  45
Lys Leu Leu Ile Tyr Ala Ala Ser Asn Leu Glu Ser Gly Ile Pro Ala
    50                  55                  60
Arg Phe Ser Gly Ser Gly Ser Gly Thr Asp Phe Thr Leu Asn Ile His
65                  70                  75                  80
Pro Val Glu Glu Glu Asp Ala Ala Thr Tyr Tyr Cys Gln Gln Ser Asp
                85                  90                  95
Glu Asn Pro Leu Thr Phe Gly Thr Gly Thr Lys Leu Glu Leu Lys Arg
            100                 105                 110
```

<210> SEQ ID NO 13
<211> LENGTH: 331
<212> TYPE: DNA
<213> ORGANISM: Artificial Sequence
<220> FEATURE:
<223> OTHER INFORMATION: Synthetic

<400> SEQUENCE: 13

```
gacattgtgc tgacccagtc tccagcttct ttggctgtgt ctctagggca gagggccacc    60
atctcctgca aggccagcca agtgttgat tatgatggtc atagttatat gaactggtac   120
caacagaaac caggacagcc acccaaactc ctcatctatg ctgcatccaa tctagaatct   180
gggatcccag ccaggtttag tggcagtggg tctgggacag acttcaccct caacatccat   240
cctgtggagg aggaggatgc tgcaacctat tactgtcagc aaagtgatga aaatcccctc   300
acgttcggta ctgggaccaa gctggagctg a                                  331
```

<210> SEQ ID NO 14
<211> LENGTH: 110
<212> TYPE: PRT
<213> ORGANISM: Artificial Sequence

```
<220> FEATURE:
<223> OTHER INFORMATION: Synthetic

<400> SEQUENCE: 14

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly His Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asp
                85                  90                  95

Glu Asn Pro Leu Thr Phe Gly Thr Gly Thr Lys Leu Glu Leu
                100                 105                 110

<210> SEQ ID NO 15
<211> LENGTH: 336
<212> TYPE: DNA
<213> ORGANISM: Artificial Sequence
<220> FEATURE:
<223> OTHER INFORMATION: Synthetic

<400> SEQUENCE: 15
gacattgtgc taacccagtc tccagcttct ttggctgtgt ctctagggca gagggccacc      60
atctcctgca aggccagcca aagtgttgat tatgatggtc atagttatat gaactggtac     120
caacagaaac caggacagcc acccaaactc ctcatctatg ctgcatccaa tctagaatct     180
gggatcccag ccaggtttag tggcagtggg tctgggacag acttcaccct caacatccat     240
cctgtggagg aggaggatgc tgcaacctat tactgtcagc aaagtgatga aaatcccctc     300
acgttcggta ctgggaccaa gctggagctg aaacgg                               336

<210> SEQ ID NO 16
<211> LENGTH: 112
<212> TYPE: PRT
<213> ORGANISM: Artificial Sequence
<220> FEATURE:
<223> OTHER INFORMATION: Synthetic

<400> SEQUENCE: 16

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly His Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asp
                85                  90                  95

Glu Asn Pro Leu Thr Phe Gly Thr Gly Thr Lys Leu Glu Leu Lys Arg
                100                 105                 110
```

<210> SEQ ID NO 17
<211> LENGTH: 365
<212> TYPE: DNA
<213> ORGANISM: Artificial Sequence
<220> FEATURE:
<223> OTHER INFORMATION: Synthetic

<400> SEQUENCE: 17

```
aggtgaagct gcagcagtca ggacctgagc tggtgaagcc tggggcttta gtgaagatat      60
cctgcaaggc ttctggttac accttcacaa gctacgatat aaattgggtg aagcagaggc     120
ctggacaggg acttgagtgg attggatgga tttatcctgg agatggtagt attaagtaca     180
atgagaaatt caagggcaag gccacactga ctgtagacaa atcctccagc acagcctaca     240
tgcaggtcag cagcctgact tctgagaatt ctgcagtcta tttctgtgca agacgggggg     300
agtatggtaa ctacgagggg gctatggact actggggcca agggaccacg gtcaccgtct     360
cctca                                                                 365
```

<210> SEQ ID NO 18
<211> LENGTH: 121
<212> TYPE: PRT
<213> ORGANISM: Artificial Sequence
<220> FEATURE:
<223> OTHER INFORMATION: Synthetic

<400> SEQUENCE: 18

```
Val Lys Leu Gln Gln Ser Gly Pro Glu Leu Val Lys Pro Gly Ala Leu
1               5                   10                  15
Val Lys Ile Ser Cys Lys Ala Ser Gly Tyr Thr Phe Thr Ser Tyr Asp
            20                  25                  30
Ile Asn Trp Val Lys Gln Arg Pro Gly Gln Gly Leu Glu Trp Ile Gly
        35                  40                  45
Trp Ile Tyr Pro Gly Asp Gly Ser Ile Lys Tyr Asn Glu Lys Phe Lys
    50                  55                  60
Gly Lys Ala Thr Leu Thr Val Asp Lys Ser Ser Ser Thr Ala Tyr Met
65                  70                  75                  80
Gln Val Ser Ser Leu Thr Ser Glu Asn Ser Ala Val Tyr Phe Cys Ala
                85                  90                  95
Arg Arg Gly Glu Tyr Gly Asn Tyr Glu Gly Ala Met Asp Tyr Trp Gly
            100                 105                 110
Gln Gly Thr Thr Val Thr Val Ser Ser
        115                 120
```

<210> SEQ ID NO 19
<211> LENGTH: 365
<212> TYPE: DNA
<213> ORGANISM: Artificial Sequence
<220> FEATURE:
<223> OTHER INFORMATION: Synthetic

<400> SEQUENCE: 19

```
aggtcaagct gcagcagtct ggacctgagc tggtgaagcc tggggcttta gtgaagatat      60
cctgcaaggc ttctggttac accttcacaa gctacgatat aaattgggtg aagcagaggc     120
ctggacaggg acttgagtgg attggatgga tttatcctgg agatggtagt attaagtaca     180
atgagaaatt caagggcaag gccacactga ctgtagacaa atcctccagc acagcctaca     240
tgcaggtcag cagcctgact tctgagaatt ctgcagtcta tttctgtgca agacgggggg     300
agtatggtaa ctacgagggg gctatggact actggggcca agggaccacg gtcaccgtct     360
cctca                                                                 365
```

<210> SEQ ID NO 20
<211> LENGTH: 121
<212> TYPE: PRT
<213> ORGANISM: Artificial Sequence
<220> FEATURE:
<223> OTHER INFORMATION: Synthetic

<400> SEQUENCE: 20

```
Val Lys Leu Gln Gln Ser Gly Pro Glu Leu Val Lys Pro Gly Ala Leu
1               5                   10                  15

Val Lys Ile Ser Cys Lys Ala Ser Gly Tyr Thr Phe Thr Ser Tyr Asp
            20                  25                  30

Ile Asn Trp Val Lys Gln Arg Pro Gly Gln Gly Leu Glu Trp Ile Gly
        35                  40                  45

Trp Ile Tyr Pro Gly Asp Gly Ser Ile Lys Tyr Asn Glu Lys Phe Lys
    50                  55                  60

Gly Lys Ala Thr Leu Thr Val Asp Lys Ser Ser Thr Ala Tyr Met
65                  70                  75                  80

Gln Val Ser Ser Leu Thr Ser Glu Asn Ser Ala Val Tyr Phe Cys Ala
                85                  90                  95

Arg Arg Gly Glu Tyr Gly Asn Tyr Gly Ala Met Asp Tyr Trp Gly
            100                 105                 110

Gln Gly Thr Thr Val Thr Val Ser Ser
        115                 120
```

<210> SEQ ID NO 21
<211> LENGTH: 365
<212> TYPE: DNA
<213> ORGANISM: Artificial Sequence
<220> FEATURE:
<223> OTHER INFORMATION: Synthetic

<400> SEQUENCE: 21

```
aggtgcagct gcaggagtct ggacctgagc tggtgaagcc tggggcttta gtgaagatat      60
cctgcaaggc ttctggttac accttcacaa gctacgatat aaattgggtg aagcagaggc     120
ctggacaggg acttgagtgg attggatgga tttatcctgg agatggtagt attaagtaca     180
atgagaaatt caagggcaag gccacactga ctgtagacaa atcctccagc acagcctaca     240
tgcaggtcag cagcctgact tctgagaatt ctgcagtcta tttctgtgca agacgggggg     300
agtatggtaa ctacgagggg gctatggact actggggcca agggaccacg gtcaccgtct     360
cctca                                                                 365
```

<210> SEQ ID NO 22
<211> LENGTH: 121
<212> TYPE: PRT
<213> ORGANISM: Artificial Sequence
<220> FEATURE:
<223> OTHER INFORMATION: Synthetic

<400> SEQUENCE: 22

```
Val Gln Leu Gln Glu Ser Gly Pro Glu Leu Val Lys Pro Gly Ala Leu
1               5                   10                  15

Val Lys Ile Ser Cys Lys Ala Ser Gly Tyr Thr Phe Thr Ser Tyr Asp
            20                  25                  30

Ile Asn Trp Val Lys Gln Arg Pro Gly Gln Gly Leu Glu Trp Ile Gly
        35                  40                  45

Trp Ile Tyr Pro Gly Asp Gly Ser Ile Lys Tyr Asn Glu Lys Phe Lys
    50                  55                  60
```

```
Gly Lys Ala Thr Leu Thr Val Asp Lys Ser Ser Thr Ala Tyr Met
 65                  70                  75                  80

Gln Val Ser Ser Leu Thr Ser Glu Asn Ser Ala Val Tyr Phe Cys Ala
                 85                  90                  95

Arg Arg Gly Glu Tyr Gly Asn Tyr Glu Gly Ala Met Asp Tyr Trp Gly
            100                 105                 110

Gln Gly Thr Thr Val Thr Val Ser Ser
        115                 120

<210> SEQ ID NO 23
<211> LENGTH: 365
<212> TYPE: DNA
<213> ORGANISM: Artificial Sequence
<220> FEATURE:
<223> OTHER INFORMATION: Synthetic

<400> SEQUENCE: 23
aggtgaagct gcagcagtct ggacctgagc tggtgaagcc tggggcttta gtgaagatat      60
cctgcaaggc ttctggttac accttcacaa gctacgatat aaattgggtg aagcagaggc     120
ctggacaggg acttgagtgg attggatgga tttatcctgg atggtagt attaagtaca       180 atgagaaatt caagggcaag gccacactga ctgtagacaa atcctccagc acagcctaca    240
tgcaggtcag cagcctgact tctgagaatt ctgcagtcta tttctgtgca agacggggga    300
agtatggtaa ctacgagggg gctatggact actggggcca agggaccacg gtcaccgtct    360
cctca                                                                 365

<210> SEQ ID NO 24
<211> LENGTH: 121
<212> TYPE: PRT
<213> ORGANISM: Artificial Sequence
<220> FEATURE:
<223> OTHER INFORMATION: Synthetic

<400> SEQUENCE: 24

Val Lys Leu Gln Gln Ser Gly Pro Glu Leu Val Lys Pro Gly Ala Leu
 1               5                  10                  15

Val Lys Ile Ser Cys Lys Ala Ser Gly Tyr Thr Phe Thr Ser Tyr Asp
                 20                  25                  30

Ile Asn Trp Val Lys Gln Arg Pro Gly Gln Gly Leu Glu Trp Ile Gly
             35                  40                  45

Trp Ile Tyr Pro Gly Asp Gly Ser Ile Lys Tyr Asn Glu Lys Phe Lys
 50                  55                  60

Gly Lys Ala Thr Leu Thr Val Asp Lys Ser Ser Thr Ala Tyr Met
 65                  70                  75                  80

Gln Val Ser Ser Leu Thr Ser Glu Asn Ser Ala Val Tyr Phe Cys Ala
                 85                  90                  95

Arg Arg Gly Glu Tyr Gly Asn Tyr Glu Gly Ala Met Asp Tyr Trp Gly
            100                 105                 110

Gln Gly Thr Thr Val Thr Val Ser Ser
        115                 120

<210> SEQ ID NO 25
<211> LENGTH: 365
<212> TYPE: DNA
<213> ORGANISM: Artificial Sequence
<220> FEATURE:
<223> OTHER INFORMATION: Synthetic

<400> SEQUENCE: 25
```

```
aggtgcagct gcagcagtca ggacctgaac tggtgaagcc tggggcttta gtgaagatat      60
cctgcaaggc ttctggttac accttcacaa gctacgatat aaattgggtg aagcagaggc     120
ctggacaggg acttgagtgg attggatgga tttatcctgg agatggtagt attaagtaca     180
atgagaaatt caagggcaag gccacactga ctgtagacaa atcctccagc acagcctaca     240
tgcaggtcag cagcctgact tctgagaatt ctgcagtcta tttctgtgca agacggggg      300 agtatggtaa ctacgagggg gctatggact actggggcca aggaccacg gtcaccgtct     360 cctca                                                                 365

<210> SEQ ID NO 26
<211> LENGTH: 121
<212> TYPE: PRT
<213> ORGANISM: Artificial Sequence
<220> FEATURE:
<223> OTHER INFORMATION: Synthetic

<400> SEQUENCE: 26

Val Gln Leu Gln Gln Ser Gly Pro Glu Leu Val Lys Pro Gly Ala Leu
1               5                   10                  15

Val Lys Ile Ser Cys Lys Ala Ser Gly Tyr Thr Phe Thr Ser Tyr Asp
            20                  25                  30

Ile Asn Trp Val Lys Gln Arg Pro Gly Gln Gly Leu Glu Trp Ile Gly
        35                  40                  45

Trp Ile Tyr Pro Gly Asp Gly Ser Ile Lys Tyr Asn Glu Lys Phe Lys
    50                  55                  60

Gly Lys Ala Thr Leu Thr Val Asp Lys Ser Ser Ser Thr Ala Tyr Met
65                  70                  75                  80

Gln Val Ser Ser Leu Thr Ser Glu Asn Ser Ala Val Tyr Phe Cys Ala
                85                  90                  95

Arg Arg Gly Glu Tyr Gly Asn Tyr Glu Gly Ala Met Asp Tyr Trp Gly
            100                 105                 110

Gln Gly Thr Thr Val Thr Val Ser Ser
        115                 120

<210> SEQ ID NO 27
<211> LENGTH: 336
<212> TYPE: DNA
<213> ORGANISM: Artificial Sequence
<220> FEATURE:
<223> OTHER INFORMATION: Synthetic

<400> SEQUENCE: 27
gacattgtgc tgacccagtc tccagcttct ttggctgtgt ctctagggca gagggccacc      60
atctcctgca aggccagcca agtgttgat tatgatggtc atagttatat gaactggtac     120
caacagaaac caggacagcc acccaaactc ctcatctatg ctgcatccaa tctagaatct     180
gggatcccag ccaggtttag tggcagtggg tctgggacag acttcaccct caacatccat     240
cctgtggagg aggaggatgc tgcaacctat tactgtcagc aaagtgatga aaatcccctc     300
acgttcggta ctgggaccaa gctggagctg aaacgg                              336

<210> SEQ ID NO 28
<211> LENGTH: 112
<212> TYPE: PRT
<213> ORGANISM: Artificial Sequence
<220> FEATURE:
<223> OTHER INFORMATION: Synthetic

<400> SEQUENCE: 28
```

```
Asp Ile Val Leu Thr Gln Ser Pro Ala Ser Leu Ala Val Ser Leu Gly
1               5                  10                 15

Gln Arg Ala Thr Ile Ser Cys Lys Ala Ser Gln Ser Val Asp Tyr Asp
            20                  25                 30

Gly His Ser Tyr Met Asn Trp Tyr Gln Gln Lys Pro Gly Gln Pro Pro
        35                  40                 45

Lys Leu Leu Ile Tyr Ala Ala Ser Asn Leu Glu Ser Gly Ile Pro Ala
    50                  55                 60

Arg Phe Ser Gly Ser Gly Ser Gly Thr Asp Phe Thr Leu Asn Ile His
65              70                  75                 80

Pro Val Glu Glu Glu Asp Ala Ala Thr Tyr Tyr Cys Gln Gln Ser Asp
                85                  90                 95

Glu Asn Pro Leu Thr Phe Gly Thr Gly Thr Lys Leu Glu Leu Lys Arg
            100                 105                110
```

<210> SEQ ID NO 29
<211> LENGTH: 365
<212> TYPE: DNA
<213> ORGANISM: Artificial Sequence
<220> FEATURE:
<223> OTHER INFORMATION: Synthetic

<400> SEQUENCE: 29

```
aggtgaagct gcagcagtct ggacctgagc tggtgaagcc tggggcttta gtgaagatat      60
cctgcaaggc ttctggttac accttcacaa gctacgatat aaattgggtg aagcagaggc     120
ctggacaggg acttgagtgg attggatgga tttatcctgg atggtagt attaagtaca      180
atgagaaatt caagggcaag gccacactga ctgtagacaa atcctccagc acagcctaca     240
tgcaggtcag cagcctgact tctgagaatt ctgcagtcta tttctgtgca agacggggg     300
agtatggtaa ctacgagggg gctatggact actggggcca aggaccacg gtcaccgtct     360
cctca                                                                365
```

<210> SEQ ID NO 30
<211> LENGTH: 121
<212> TYPE: PRT
<213> ORGANISM: Artificial Sequence
<220> FEATURE:
<223> OTHER INFORMATION: Synthetic

<400> SEQUENCE: 30

```
Val Lys Leu Gln Gln Ser Gly Pro Glu Leu Val Lys Pro Gly Ala Leu
1               5                  10                 15

Val Lys Ile Ser Cys Lys Ala Ser Gly Tyr Thr Phe Thr Ser Tyr Asp
            20                  25                 30

Ile Asn Trp Val Lys Gln Arg Pro Gly Gln Gly Leu Glu Trp Ile Gly
        35                  40                 45

Trp Ile Tyr Pro Gly Asp Gly Ser Ile Lys Tyr Asn Glu Lys Phe Lys
    50                  55                 60

Gly Lys Ala Thr Leu Thr Val Asp Lys Ser Ser Ser Thr Ala Tyr Met
65              70                  75                 80

Gln Val Ser Ser Leu Thr Ser Glu Asn Ser Ala Val Tyr Phe Cys Ala
                85                  90                 95

Arg Arg Gly Glu Tyr Gly Asn Tyr Glu Gly Ala Met Asp Tyr Trp Gly
            100                 105                110

Gln Gly Thr Thr Val Thr Val Ser Ser
        115                 120
```

```
<210> SEQ ID NO 31
<211> LENGTH: 365
<212> TYPE: DNA
<213> ORGANISM: Artificial Sequence
<220> FEATURE:
<223> OTHER INFORMATION: Synthetic

<400> SEQUENCE: 31
aggtgcagct gcagcagtca ggacctgaac tggtgaagcc tggggcttta gtgaagatat      60
cctgcaaggc ttctggttac accttcacaa gctacgatat aaattgggtg aagcagaggc     120
ctggacaggg acttgagtgg attggatgga tttatcctgg agatggtagt attaagtaca     180
atgagaaatt caagggcaag gccacactga ctgtagacaa atcctccagc acagcctaca     240
tgcaggtcag cagcctgact tctgagaatt ctgcagtcta tttctgtgca agacggggga     300
agtatggtaa ctacgagggg gctatggact actggggcca agggaccacg gtcaccgtct     360
cctca                                                                  365

<210> SEQ ID NO 32
<211> LENGTH: 121
<212> TYPE: PRT
<213> ORGANISM: Artificial Sequence
<220> FEATURE:
<223> OTHER INFORMATION: Synthetic

<400> SEQUENCE: 32

Val Gln Leu Gln Gln Ser Gly Pro Glu Leu Val Lys Pro Gly Ala Leu
1               5                   10                  15

Val Lys Ile Ser Cys Lys Ala Ser Gly Tyr Thr Phe Thr Ser Tyr Asp
            20                  25                  30

Ile Asn Trp Val Lys Gln Arg Pro Gly Gln Gly Leu Glu Trp Ile Gly
        35                  40                  45

Trp Ile Tyr Pro Gly Asp Gly Ser Ile Lys Tyr Asn Glu Lys Phe Lys
    50                  55                  60

Gly Lys Ala Thr Leu Thr Val Asp Lys Ser Ser Ser Thr Ala Tyr Met
65                  70                  75                  80

Gln Val Ser Ser Leu Thr Ser Glu Asn Ser Ala Val Tyr Phe Cys Ala
                85                  90                  95

Arg Arg Gly Glu Tyr Gly Asn Tyr Glu Gly Ala Met Asp Tyr Trp Gly
            100                 105                 110

Gln Gly Thr Thr Val Thr Val Ser Ser
        115                 120

<210> SEQ ID NO 33
<211> LENGTH: 122
<212> TYPE: PRT
<213> ORGANISM: Artificial Sequence
<220> FEATURE:
<223> OTHER INFORMATION: Synthetic

<400> SEQUENCE: 33

Gln Val Gln Leu Gln Gln Ser Gly Pro Glu Leu Val Lys Pro Gly Ala
1               5                   10                  15

Leu Val Lys Ile Ser Cys Lys Ala Ser Gly Tyr Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Tyr Pro Gly Asp Gly Ser Ile Lys Tyr Asn Glu Lys Phe
    50                  55                  60
```

```
Lys Gly Lys Ala Thr Leu Thr Val Asp Lys Ser Ser Thr Ala Tyr
 65                  70                  75                  80

Met Gln Val Ser Ser Leu Thr Ser Glu Asn Ser Ala Val Tyr Phe Cys
                 85                  90                  95

Ala Arg Arg Gly Glu Tyr Gly Asn Tyr Glu Gly Ala Met Asp Tyr Trp
            100                 105                 110

Gly Gln Gly Thr Thr Val Thr Val Ser Ser
        115                 120

<210> SEQ ID NO 34
<211> LENGTH: 25
<212> TYPE: PRT
<213> ORGANISM: Artificial Sequence
<220> FEATURE:
<223> OTHER INFORMATION: Synthetic

<400> SEQUENCE: 34

Asp Ile Val Leu Thr Gln Ser Pro Ala Ser Leu Ala Val Ser Leu Gly
 1               5                  10                  15

Gln Arg Ala Thr Ile Ser Ser Lys Ala
            20                  25

<210> SEQ ID NO 35
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (21)..(21)
<223> OTHER INFORMATION: Xaa = Cys or any naturally occurring amino acid

<400> SEQUENCE: 35

Val Gln Leu Gln Gln Ser Gly Pro Glu Leu Val Lys Pro Gly Ala Leu
 1               5                  10                  15

Val Lys Ile Ser Xaa Lys Ala Ser Gly
            20                  25

<210> SEQ ID NO 36
<211> LENGTH: 111
<212> TYPE: PRT
<213> ORGANISM: Artificial Sequence
<220> FEATURE:
<223> OTHER INFORMATION: Synthetic

<400> SEQUENCE: 36

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Ser Val Asp Tyr Asp
            20                  25                  30

Gly His Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asp
                 85                  90                  95

Glu Asn Pro Leu Thr Phe Gly Gly Gly Thr Lys Val Glu Ile Lys
            100                 105                 110
```

```
<210> SEQ ID NO 37
<211> LENGTH: 111
<212> TYPE: PRT
<213> ORGANISM: Artificial Sequence
<220> FEATURE:
<223> OTHER INFORMATION: Synthetic

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly His Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asp
                85                  90                  95

Glu Asn Pro Leu Thr Phe Gly Gly Gly Thr Lys Val Glu Ile Lys
            100                 105                 110

<210> SEQ ID NO 38
<211> LENGTH: 111
<212> TYPE: PRT
<213> ORGANISM: Artificial Sequence
<220> FEATURE:
<223> OTHER INFORMATION: Synthetic

<400> SEQUENCE: 38

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly His Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asp
                85                  90                  95

Glu Asn Pro Leu Thr Phe Gly Gly Gly Thr Lys Val Glu Ile Lys
            100                 105                 110

<210> SEQ ID NO 39
<211> LENGTH: 111
<212> TYPE: PRT
<213> ORGANISM: Artificial Sequence
<220> FEATURE:
<223> OTHER INFORMATION: Synthetic

<400> SEQUENCE: 39

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly His Ser Tyr Met Asn Trp Tyr Gln Gln Lys Pro Gly Lys Ala Pro
        35                  40                  45
```

Lys Leu Leu Ile Tyr Ala Ala Ser Asn Leu Glu Ser Gly Ile Pro Ser
            50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asp
                85                  90                  95

Glu Asn Pro Leu Thr Phe Gly Gly Gly Thr Lys Val Glu Ile Lys
               100                 105                 110

<210> SEQ ID NO 40
<211> LENGTH: 122
<212> TYPE: PRT
<213> ORGANISM: Artificial Sequence
<220> FEATURE:
<223> OTHER INFORMATION: Synthetic

<400> SEQUENCE: 40

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Phe Thr Ser Tyr
                20                  25                  30

Asp Ile Asn Trp Val Arg Gln Ala Pro Gly Lys Gly Leu Glu Trp Met
            35                  40                  45

Gly Trp Ile Tyr Pro Gly Asp Gly Ser Ile Lys Tyr Asn Glu Lys Phe
        50                  55                  60

Lys Gly Arg Val Thr Met Thr Val Asp Lys Ser Thr Asp Thr Ala Tyr
 65                  70                  75                  80

Met Glu Leu Ser Ser Leu Arg Ser Glu Asp Thr Ala Val Tyr Tyr Cys
                85                  90                  95

Ala Arg Arg Gly Glu Tyr Gly Asn Tyr Glu Gly Ala Met Asp Tyr Trp
               100                 105                 110

Gly Gln Gly Thr Leu Val Thr Val Ser Ser
               115                 120

<210> SEQ ID NO 41
<211> LENGTH: 122
<212> TYPE: PRT
<213> ORGANISM: Artificial Sequence
<220> FEATURE:
<223> OTHER INFORMATION: Synthetic

<400> SEQUENCE: 41

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Phe Thr Ser Tyr
                20                  25                  30

Asp Ile Asn Trp Val Arg Gln Ala Pro Gly Lys Gly Leu Glu Trp Met
            35                  40                  45

Gly Trp Ile Tyr Pro Gly Asp Gly Ser Ile Lys Tyr Asn Glu Lys Phe
        50                  55                  60

Lys Gly Arg Val Thr Met Thr Val Asp Lys Ser Thr Asp Thr Ala Tyr
 65                  70                  75                  80

Met Glu Leu Ser Ser Leu Arg Ser Glu Asp Thr Ala Val Tyr Tyr Cys
                85                  90                  95

Ala Arg Arg Gly Glu Tyr Gly Asn Tyr Glu Gly Ala Met Asp Tyr Trp
               100                 105                 110

Gly Gln Gly Thr Leu Val Thr Val Ser Ser
               115                 120

-continued

<210> SEQ ID NO 42
<211> LENGTH: 122
<212> TYPE: PRT
<213> ORGANISM: Artificial Sequence
<220> FEATURE:
<223> OTHER INFORMATION: Synthetic

<400> SEQUENCE: 42

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Tyr
            20                  25                  30

Asp Ile Asn Trp Val Arg Gln Ala Pro Gly Lys Gly Leu Glu Trp Ile
        35                  40                  45

Gly Trp Ile Tyr Pro Gly Asp Gly Ser Ile Lys Tyr Asn Glu Lys Phe
    50                  55                  60

Lys Gly Lys Ala Thr Leu Thr Val Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Glu Tyr Gly Asn Tyr Glu Gly Ala Met Asp Tyr Trp
            100                 105                 110

Gly Gln Gly Thr Leu Val Thr Val Ser Ser
        115                 120
```

<210> SEQ ID NO 43
<211> LENGTH: 122
<212> TYPE: PRT
<213> ORGANISM: Artificial Sequence
<220> FEATURE:
<223> OTHER INFORMATION: Synthetic

<400> SEQUENCE: 43

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Tyr
            20                  25                  30

Asp Ile Asn Trp Val Arg Gln Ala Pro Gly Lys Gly Leu Glu Trp Ile
        35                  40                  45

Gly Trp Ile Tyr Pro Gly Asp Gly Ser Ile Lys Tyr Asn Glu Lys Phe
    50                  55                  60

Lys Gly Lys Ala Thr Leu Thr Val Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Glu Tyr Gly Asn Tyr Glu Gly Ala Met Asp Tyr Trp
            100                 105                 110

Gly Gln Gly Thr Leu Val Thr Val Ser Ser
        115                 120
```

<210> SEQ ID NO 44
<211> LENGTH: 111
<212> TYPE: PRT
<213> ORGANISM: Artificial Sequence
<220> FEATURE:
<223> OTHER INFORMATION: Synthetic

<400> SEQUENCE: 44

```
Asp Ile Val Leu Thr Gln Asp Pro Ala Ser Leu Ala Val Ser Leu Gly
1               5                   10                  15
```

Gln Arg Ala Thr Ile Ser Cys Lys Ala Ser Gln Ser Val Asp Tyr Asp
            20                  25                  30

Gly His Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asp
                85                  90                  95

Glu Asn Pro Leu Thr Phe Gly Thr Gly Thr Lys Leu Glu Leu Lys
            100                 105                 110

<210> SEQ ID NO 45
<211> LENGTH: 107
<212> TYPE: PRT
<213> ORGANISM: Artificial Sequence
<220> FEATURE:
<223> OTHER INFORMATION: Synthetic

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 46
<211> LENGTH: 111
<212> TYPE: PRT
<213> ORGANISM: Artificial Sequence
<220> FEATURE:
<223> OTHER INFORMATION: Synthetic

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly His Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asp
                85                  90                  95

Glu Asn Pro Leu Thr Phe Gly Gly Gly Thr Lys Val Glu Ile Lys
            100                 105                 110

<210> SEQ ID NO 47
<211> LENGTH: 111
<212> TYPE: PRT
<213> ORGANISM: Artificial Sequence
<220> FEATURE:
<223> OTHER INFORMATION: Synthetic

<400> SEQUENCE: 47

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly His Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asp
                85                  90                  95

Glu Asn Pro Leu Thr Phe Gly Gly Gly Thr Lys Val Glu Ile Lys
            100                 105                 110

<210> SEQ ID NO 48
<211> LENGTH: 122
<212> TYPE: PRT
<213> ORGANISM: Artificial Sequence
<220> FEATURE:
<223> OTHER INFORMATION: Synthetic

<400> SEQUENCE: 48

Gln Val Gln Leu Gln Gln Ser Gly Pro Glu Leu Val Lys Pro Gly Ala
1               5                   10                  15

Leu Val Lys Ile Ser Cys Lys Ala Ser Gly Tyr Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Tyr Pro Gly Asp Gly Ser Ile Lys Tyr Asn Glu Lys Phe
    50                  55                  60

Lys Gly Lys Ala Thr Leu Thr Val Asp Lys Ser Ser Ser Thr Ala Tyr
65                  70                  75                  80

Met Gln Val Ser Ser Leu Thr Ser Glu Asn Ser Ala Val Tyr Phe Cys
                85                  90                  95

Ala Arg Arg Gly Glu Tyr Gly Asn Tyr Glu Gly Ala Met Asp Tyr Trp
            100                 105                 110

Gly Gln Gly Thr Thr Val Thr Val Ser Ser
        115                 120

<210> SEQ ID NO 49
<211> LENGTH: 121
<212> TYPE: PRT
<213> ORGANISM: Artificial Sequence
<220> FEATURE:
<223> OTHER INFORMATION: Synthetic

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu

```
                    20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Val Gly Arg Cys Ser Ser Thr Ser Cys Asp Tyr Trp Gly
            100                 105                 110

Gln Gly Thr Leu Val Thr Val Ser Ser
        115                 120

<210> SEQ ID NO 50
<211> LENGTH: 122
<212> TYPE: PRT
<213> ORGANISM: Artificial Sequence
<220> FEATURE:
<223> OTHER INFORMATION: Synthetic

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Tyr
            20                  25                  30

Asp Ile Asn Trp Val Arg Gln Ala Pro Gly Lys Gly Leu Glu Trp Met
        35                  40                  45

Gly Trp Ile Tyr Pro Gly Asp Gly Ser Ile Lys Tyr Asn Glu Lys Phe
    50                  55                  60

Lys Gly Arg Val Thr Met Thr Val Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Glu Tyr Gly Asn Tyr Glu Gly Ala Met Asp Tyr Trp
            100                 105                 110

Gly Gln Gly Thr Leu Val Thr Val Ser Ser
        115                 120

<210> SEQ ID NO 51
<211> LENGTH: 122
<212> TYPE: PRT
<213> ORGANISM: Artificial Sequence
<220> FEATURE:
<223> OTHER INFORMATION: Synthetic

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Tyr
            20                  25                  30

Asp Ile Asn Trp Val Arg Gln Ala Pro Gly Lys Gly Leu Glu Trp Ile
        35                  40                  45

Gly Trp Ile Tyr Pro Gly Asp Gly Ser Ile Lys Tyr Asn Glu Lys Phe
    50                  55                  60

Lys Gly Lys Ala Thr Leu Thr Val Asp Lys Ser Thr Asp Thr Ala Tyr
65                  70                  75                  80

Met Glu Leu Ser Ser Leu Arg Ser Glu Asp Thr Ala Val Tyr Tyr Cys
```

|   |   |   |   |   | 85 |   |   |   | 90 |   |   |   |   | 95 |
|---|---|---|---|---|---|---|---|---|---|---|---|---|---|---|
Ala Arg Arg Gly Glu Tyr Gly Asn Tyr Glu Gly Ala Met Asp Tyr Trp
            100                 105                 110

Gly Gln Gly Thr Leu Val Thr Val Ser Ser
        115                 120

<210> SEQ ID NO 52
<211> LENGTH: 333
<212> TYPE: DNA
<213> ORGANISM: Artificial Sequence
<220> FEATURE:
<223> OTHER INFORMATION: Synthetic

<400> SEQUENCE: 52
gacatccaga tgacccagtc tccatcctcc ctgtctgcat ctgtaggaga cagagtcacc      60
atcacttgca aggccagcca gagcgttgat tatgatggtc atagttatat gaactggtat     120
cagcagaaac cagggaaagc ccctaagctc ctgatctatg ctgcatccaa tttggaatct     180
ggggtcccat caaggttcag tggcagtgga tctgggacag atttcactct caccatcagc     240
agtctgcaac tgaagatttt gcaacttac tactgtcagc aaagtgatga aaatccctc       300 actttcggcg agggaccaa ggtggagatc aaa                                   333

<210> SEQ ID NO 53
<211> LENGTH: 333
<212> TYPE: DNA
<213> ORGANISM: Artificial Sequence
<220> FEATURE:
<223> OTHER INFORMATION: Synthetic

<400> SEQUENCE: 53
gacattcaga tgacccagtc tccatcctct ttgtctgcat ctgtagggga cagggtcacc      60
atcacttgca aggccagcca gagcgttgat tatgatggtc atagttatat gaactggtac     120
caacagaaac caggaaaagc ccccaaactc ctcatctatg ctgcatccaa tttggaatct     180
ggggtcccat caaggtttag tggcagtggg tctgggacag acttcaccct caccatcagc     240
agtctgcaac tgaggatttt gcaacctat tactgtcagc aaagtgatga aaatccctc       300 actttcggtg agggaccaa ggtggagatc aaa                                   333

<210> SEQ ID NO 54
<211> LENGTH: 333
<212> TYPE: DNA
<213> ORGANISM: Artificial Sequence
<220> FEATURE:
<223> OTHER INFORMATION: Synthetic

<400> SEQUENCE: 54
gacatccagc tgacccagtc tccatcctcc ctgtctgcat ctgtaggaga cagagtcacc      60
atcacttgca aggccagcca gagcgttgat tatgatggtc atagttatat gaactggtat     120
cagcagaaac cagggaaagc ccctaagctc ctgatctatg ctgcatccaa tttggaatct     180
gggatcccat caaggttcag tggcagtgga tctgggacag atttcactct caccatcagc     240
agtctgcaac tgaagatttt gcaacttac tactgtcagc aaagtgatga aaatccctc       300 actttcggcg agggaccaa ggtggagatc aaa                                   333

<210> SEQ ID NO 55
<211> LENGTH: 333
<212> TYPE: DNA
<213> ORGANISM: Artificial Sequence
<220> FEATURE:

<223> OTHER INFORMATION: Synthetic

<400> SEQUENCE: 55

| gacattcagc tgacccagtc tccatcctct ttgtctgcat ctgtagggga cagggtcacc | 60 |
| atcacttgca aggccagcca gagcgttgat tatgatggtc atagttatat gaactggtac | 120 |
| caacagaaac caggaaaagc ccccaaactc ctcatctatg ctgcatccaa tttggaatct | 180 |
| gggatcccat caaggtttag tggcagtggg tctgggacag acttcaccct caccatcagc | 240 |
| agtctgcaac ctgaggattt tgcaacctat tactgtcagc aaagtgatga aaatcccctc | 300 |
| actttcggtg agggaccaa ggtggagatc aaa | 333 |

<210> SEQ ID NO 56
<211> LENGTH: 366
<212> TYPE: DNA
<213> ORGANISM: Artificial Sequence
<220> FEATURE:
<223> OTHER INFORMATION: Synthetic

<400> SEQUENCE: 56

| caggtccagc tggtacagtc tggggctgag gtgaagaagc ctggggcctc agtgaaggtc | 60 |
| tcctgcaagg tttccggata caccttcact agctacgata taaattgggt gcgacaggct | 120 |
| cctggaaaag ggcttgagtg gatgggatgg atttatcctg agatggtag cattaagtac | 180 |
| aatgagaaat tcaagggcag agtcaccatg accgtagaca atctacaga cacagcctac | 240 |
| atggagctga gcagcctgag atctgaggac acagccgtgt attactgtgc aagacggggg | 300 |
| gagtatggta actacgaggg ggctatggac tactggggcc agggaaccct ggtcaccgtc | 360 |
| tcctca | 366 |

<210> SEQ ID NO 57
<211> LENGTH: 366
<212> TYPE: DNA
<213> ORGANISM: Artificial Sequence
<220> FEATURE:
<223> OTHER INFORMATION: Synthetic

<400> SEQUENCE: 57

| caggtgcagc tggtacagtc aggagctgaa gtgaagaagc ctgggcttc agtgaaggtc | 60 |
| tcctgcaagg tttctggtta caccttcaca agctacgata taaattgggt gcgacaggct | 120 |
| cctggaaaag gacttgagtg gatgggatgg atttatcctg agatggtag cattaagtac | 180 |
| aatgagaaat tcaagggcag agtcacaatg actgtagaca atccacaga cacagcctac | 240 |
| atggagctga gcagcctgag atctgaggac acagcagtct attactgtgc aagacggggg | 300 |
| gagtatggta actacgaggg ggctatggac tactggggcc aagggaccct ggtcaccgtc | 360 |
| tcctca | 366 |

<210> SEQ ID NO 58
<211> LENGTH: 366
<212> TYPE: DNA
<213> ORGANISM: Artificial Sequence
<220> FEATURE:
<223> OTHER INFORMATION: Synthetic

<400> SEQUENCE: 58

| caggtccagc tggtacagtc tggggctgag gtgaagaagc ctggggcctc agtgaaggtc | 60 |
| tcctgcaagg tttccggata caccttcact agctacgata taaattgggt gcgacaggct | 120 |
| cctggaaaag ggcttgagtg gattggatgg atttatcctg agatggtag cattaagtac | 180 |

```
aatgagaaat tcaagggcaa ggccaccctg accgtagaca aatctacaga cacagcctac      240
atggagctga gcagcctgag atctgaggac acagccgtgt attactgtgc aagacggggg      300
gagtatggta actacgaggg ggctatggac tactggggcc agggaaccct ggtcaccgtc      360
tcctca                                                                366

<210> SEQ ID NO 59
<211> LENGTH: 366
<212> TYPE: DNA
<213> ORGANISM: Artificial Sequence
<220> FEATURE:
<223> OTHER INFORMATION: Synthetic

<400> SEQUENCE: 59
caggtgcagc tggtacagtc aggagctgaa gtgaagaagc ctggggcttc agtgaaggtc       60
tcctgcaagg tttctggtta caccttcaca agctacgata taaattgggt gcgacaggct      120
cctggaaaag gacttgagtg gattggatgg atttatcctg gagatggtag cattaagtac      180
aatgagaaat tcaagggcaa ggccacactg actgtagaca aatccacaga cacagcctac      240
atggagctga gcagcctgag atctgaggac acagcagtct attactgtgc aagacggggg      300
gagtatggta actacgaggg ggctatggac tactggggcc aagggaccct ggtcaccgtc      360
tcctca                                                                366
```

ANTI-P-SELECTIN ANTIBODIES AND METHODS OF USING THE SAME TO TREAT INFLAMMATORY DISEASES

FIELD OF THE INVENTION

The invention relates to antibodies, e.g., chimeric or humanized antibodies, which recognize (i.e., bind) P-selectin and which are useful for the treatment of inflammatory and thrombotic conditions, e.g., sickle cell disease, pain associated with sickle cell disease, deep vein thrombosis, asthma, rheumatoid arthritis, psoriasis, and ischemia reperfusion injury.

BACKGROUND OF THE INVENTION

Selectins, particularly P-selectin, contribute to many inflammatory and thrombotic diseases, such as deep venous thrombosis (DVT), arthritis, asthma, psoriasis, and vasoocclusive crisis in sickle cell anemia. For example, patients with sickle cell anemia suffer vasoocclusive complications in which sickled red cells clump in small vessels blocking blood flow (ischemia) to downstream organs. This causes patients intense pain and repeated hospitalizations. It can also lead to progressive multi-organ dysfunction and premature death. Murine models of sickle cell anemia have been developed by introduction of transgenes for the human globin proteins, one of which has the mutation found in sickle cell anemia. These mice have sickled red cells and develop vasoocclusive complications. The adherence of sickle red blood cells (RBCs) to the vascular endothelium appears to contribute to vaso-occlusion observed in sickle cell disease. Using genetically-engineered mice as a model for human sickle cell disease it was shown that there is a selectin-dependent recruitment of leukocytes to inflamed microvessels, where they interact with sickled red cells. Sickle cell mice exposed to hypoxia followed by reoxygenation had higher leukocyte rolling and lower RBC velocities in small vessels compared to controls. Injection of an anti-P-selectin monoclonal antibody at the time of reoxygenation not only prevented the increase in these parameters, it also reduced leukocyte rolling and increased RBC velocities to levels that approached those in unchallenged control mice. This indicates that a reduction in leukocyte adhesion can be accomplished by preventing P-selectin activity, thereby resulting in improved microcirculatory blood flow.

P-selectin has also been implicated in other disease processes, such as tissue and organ damage associated with inflammation, e.g., ischemia-reperfusion injury. Thus, P-selectin is a target for intervention in human inflammatory and thrombotic diseases. Accordingly, there is a need for treatments that target P-selectin as a means of treating inflammatory and thrombotic diseases.

SUMMARY OF THE INVENTION

A first aspect of the invention features an antibody (e.g., a chimeric or a humanized antibody) having an immunoglobulin light chain variable region having a sequence selected from the group consisting of KASQSVDYDGHSYMN (SEQ ID NO: 1), AASNLES (SEQ ID NO: 2), or QQSDENPLT (SEQ ID NO: 3). In an embodiment, the constant region or the framework region (i.e., the non-variable region(s) of the antibody is from a human antibody.

A second aspect of the invention features an antibody (e.g., a chimeric or a humanized antibody) having an immunoglobulin heavy chain variable region comprising a sequence selected from the group consisting of SYDIN (SEQ ID NO: 4), WIYPGDGSIKYNEKFKG (SEQ ID NO: 5), or RGEYGNYEGAMDY (SEQ ID NO: 6). In a further embodiment, the antibody further includes a light chain variable region having a sequence selected from the group consisting of KASQSVDYDGHSYMN (SEQ ID NO: 1), AASNLES (SEQ ID NO: 2), or QQSDENPLT (SEQ ID NO: 3). In an embodiment, the antibody has:

a. a light chain variable region having, in sequential order, a first complementarity determining region (CDR) having the sequence KASQSVDYDGHSYMN (SEQ ID NO: 1), a second CDR having the sequence AASNLES (SEQ ID NO: 2), and a third CDR having the sequence QQSDENPLT (SEQ ID NO: 3); and b. a heavy chain variable region having, in sequential order, a first CDR having the sequence SYDIN (SEQ ID NO: 4), a second CDR having the sequence WIYPGDGSIKYNEKFKG (SEQ ID NO: 5), and a third CDR having the sequence RGEYGNYEGAMDY (SEQ ID NO: 6). In another embodiment, the constant region or the framework region (i.e., the non-variable region(s) of the antibody is from a human antibody.

A third aspect of the invention features an antibody (e.g., a chimeric or humanized antibody) having an immunoglobulin light chain variable region having a sequence having at least 90% sequence identity to a sequence set forth in SEQ ID NO: 36, SEQ ID NO: 37, SEQ ID NO: 38, or SEQ ID NO: 39.

A fourth aspect of the invention features an antibody (e.g., a chimeric or a humanized antibody) having an immunoglobulin heavy chain variable region having a sequence having at least 90% sequence identity to a sequence set forth in SEQ ID NO: 40, SEQ ID NO: 41, SEQ ID NO: 42, or SEQ ID NO: 43. In an embodiment, the antibody further includes a light chain variable region having a sequence having at least 90% sequence identity to a sequence set forth in SEQ ID NO: 36, SEQ ID NO: 37, SEQ ID NO: 38, or SEQ ID NO: 39.

A fifth aspect of the invention features a method of treating or preventing an inflammatory or thrombotic condition (e.g., sickle cell disease or pain crisis associated with sickle cell disease; deep vein thrombosis; asthma; rheumatoid arthritis; psoriasis; ischemia reperfusion injury; ischemia reperfusion injury caused by stroke; ischemia reperfusion injury caused by myocardial infarction; or ischemia reperfusion injury caused by organ transplantation) comprising administering the antibody of any one of the first, second, third, or fourth aspects of the invention to a subject in need of treatment in an amount sufficient to treat or prevent said inflammatory or thrombotic condition. In an embodiment of the invention, the antibody is administered to the subject intravenously; subcutaneously; topically; intradermally; intramuscularly; intraperitoneally; intranasally; epidurally; or orally. In another embodiment, the antibody is admixed with a pharmaceutically acceptable excipient. In another embodiment, the pharmaceutical composition is administered to the subject in an amount sufficient to treat or prevent the inflammatory or thrombotic condition.

A sixth aspect of the invention features a kit that includes the pharmaceutical composition of the fifth aspect of the invention (e.g., in a vial or other container) and instructions for treating an inflammatory or thrombotic condition by administering the pharmaceutical composition.

A seventh aspect of the invention features a nucleic acid encoding an immunoglobulin light chain variable region having a nucleic acid sequence having at least 90% sequence identity to a sequence set forth in any one of SEQ ID NO: 7, 9, 11, 13, 15, or 27.

An eighth aspect of the invention features a nucleic acid encoding an immunoglobulin heavy chain variable region having a nucleic acid sequence having at least 90% sequence identity to a sequence set forth in any one of SEQ ID NO: 17, 19, 21, 23, 25, 29, or 31. In an embodiment, the nucleic acid further encodes a nucleic acid sequence having at least 90% sequence identity to a sequence set forth in any one of SEQ ID NO: 7, 9, 11, 13, 15, or 27 that encodes a light chain variable region.

In several embodiments of all aspects of the invention, the antibody binds P-selectin with a dissociation constant less than $10^{-7}$ M, preferably less than $10^{-8}$M, $10^{-9}$M, $10^{-10}$M, $10^{-11}$M, and $10^{-12}$M, and most preferably less than $10^{-13}$M. In other embodiments, the antibody has a dissociation constant between $10^{-7}$ M and $10^{-13}$ M. In other embodiments of the first and second aspects of the invention, the antibody is humanized. In other embodiments, the antibody is recombinantly produced. In yet other embodiments, the antibody is an immunoglobulin selected from the group consisting of immunoglobulin A, immunoglobulin D, immunoglobulin E, immunoglobulin G, or immunoglobulin M.

By "chimeric antibody" means an antibody having light and heavy chain genes which have been constructed, typically by genetic engineering, from immunoglobulin variable and/or constant region genes belonging to one or more different species. For example, the variable segments of the genes (or, e.g., one or more of the complementarity determining regions (CDRs) within the variable regions) from, e.g., a mouse antibody (e.g., a monoclonal or polyclonal antibody), may be used in conjuction with human constant segments to produce the chimeric antibody. A typical therapeutic chimeric antibody is thus a hybrid protein composed of the variable or antigen-binding domain from a mouse antibody (e.g., one or more of the CDRs of a mouse antibody) and the constant or effector domain from a human antibody, although other mammalian species may be used. The chimeric antibody can also include amino acid sequence obtained from a protein source other than an antibody.

By "complementarity determining region" or "CDR" is meant an amino acid sequence, or a nucleic acid sequence encoding the amino acid sequence, of an antibody which is the hypervariable region of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs).

The variable regions of each light/heavy chain pair form the antibody binding site. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. CDR and FR residues are delineated according to the standard sequence definition of Kabat et al. (Sequences of Proteins of Immunological Interest (National Institutes of Health, Bethesda, Md. (1987) and (1991). An alternative structural definition has been proposed by Chothia et al., J. Mol. Biol. 196:901-917 (1987); Nature 342:878-883 (1989); and J. Mol. Biol. 186: 651-663 (1989)).

By "humanized antibody" means a type of chimeric antibody comprising a human framework region and one or more CDRs from a non-human (usually a mouse or rat) immunoglobulin. The non-human immunoglobulin providing the CDRs is called the "donor" and the human immunoglobulin providing the framework is called the "acceptor". Constant regions need not be present, but if they are, they should be substantially identical to human immunoglobulin constant regions, i.e., at least about 85-90%, preferably about 95% or more identical. Hence, all parts of a humanized immunoglobulin, except possibly the CDRs, are substantially identical to corresponding parts of natural human immunoglobulin sequences.

It is understood that the antibodies of the present invention may have additional conservative amino acid substitutions which have substantially no effect on antigen binding or other immunoglobulin functions. By conservative substitutions is intended combinations such as gly, ala; val, ile, leu; asp, glu; asn, gln; ser, thr; lys, arg; and phe, tyr. Antibodies of the present invention may also include a framework that is identical to the framework of a particular human immunoglobulin chain, the acceptor, and three CDRs from a non-human donor immunoglobulin chain. Alternatively, one or more additional amino acids in the framework can be changed to be the same as amino acids in other human framework regions. The present invention includes antibodies in which changes of a limited number of amino acids in the framework of a humanized immunoglobulin chain are made so that the amino acids from the donor rather than from the acceptor are used at those positions, so as to increase the affinity of the antibody (see, e.g., Queen et al., Proc. Natl. Acad Sci USA, 86:10029-10032, 1989; and Hodgson et al., Bio/Technology, 9:421, 1991).

By "donor" is meant a nucleic acid sequence that encodes, or an amino acid sequence from, a protein, e.g., an antibody (polyclonal, monoclonal, or recombinant), which amino acid sequence contributes the sequences of the variable regions, e.g., the CDRs, of an antibody of the invention.

By "acceptor" is meant a nucleic acid sequence that encodes, or an amino acid sequence from, a protein, e.g., an antibody (polyclonal, monoclonal, or recombinant), which amino acid sequence contributes the sequences of the constant regions of an antibody of the invention and/or the framework regions supporting the CDRs. Preferably a human antibody provides the acceptor sequences for an antibody of the invention.

As applied to polypeptides, the term "sequence identity" means peptides that share identical amino acids at corresponding positions. The term "sequence similarity" means peptides that have identical or similar amino acids (i.e., conservative substitutions) at corresponding positions. The term "substantial identity" means that two peptide sequences, when optimally aligned, such as by the programs GAP or BESTFIT using default gap weights, share at least 80% sequence identity, preferably at least 90% sequence identity, more preferably at least 95% sequence identity or more (e.g., 99% sequence identity). Preferably, residue positions which are not identical differ by conservative amino acid substitutions. The term "substantial similarity" means that two peptide sequences share corresponding percentages of sequence similarity.

The term "substantially pure", in regard to an antibody of the invention, means that it is the predominant species present (i.e., on a molar basis it is more abundant than any other individual species in the composition), and preferably a substantially purified fraction is a composition wherein the object species, i.e., an antibody of the invention, comprises at least about 50% (on a molar basis), preferably 60%, 70%, 80%, 90%, or 95% or more of all macromolecular species present. Generally, a substantially pure composition will comprise more than about 80 to 90% of all macromolecular species present in the composition. Most preferably, the object species is purified to essential homogeneity (contaminant species cannot be detected in the composition by conventional detection methods) wherein the composition consists essentially of a single macromolecular species.

For purposes of classifying amino acids substitutions as conservative or nonconservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for another.

Amino acids from the variable regions of the mature heavy and light chains of immunoglobulins are designated Hx and Lxx respectively, where x is a number designating the position of an amino acids according to the scheme of Kabat et al., Sequences of Proteins of Immunological Interest (National Institutes of Health, Bethesda, Md. (1987) and (1991)) (hereinafter collectively referred to as "Kabat et al.," incorporated by reference in their entirety for all purposes). Kabat et al. list many amino acid sequences for antibodies for each subclass, and list the most commonly occurring amino acid for each residue position in that subclass. Kabat et al. use a method for assigning a residue number to each amino acid in a listed sequence, and this method for assigning residue numbers has become standard in the field. Kabat et al.'s scheme is extendible to other antibodies not included in the compendium by aligning the antibody in question with one of the consensus sequences in Kabat et al. The use of the Kabat et al. numbering system readily identifies amino acids at equivalent positions in different antibodies. For example, an amino acid at the L50 position of a human antibody occupies the equivalence position to an amino acid position L50 of a mouse antibody.

"Immunoglobulin," "antibody" or "antibody peptide(s)" refers to an intact antibody or a binding fragment thereof that competes with the intact antibody for specific binding to P-selectin.

"Substantial inhibition" means at least about 50% inhibition, preferably about 60% to about 80%, and more usually about greater than 85% or more (as measured in an in vitro competitive binding assay).

The invention provides compositions and methods for the treatment of a host of inflammatory and thrombotic conditions including, e.g., sickle cell disease or pain crisis associated with sickle cell disease, deep vein thrombosis, asthma, rheumatoid arthritis, psoriasis, and ischemia reperfusion injury. Other features and advantages of the invention will be apparent from the following Detailed Description, the drawings, and the claims.

BRIEF DESCRIPTION OF THE DRAWINGS

FIG. 1 is a schematic showing proposed humanized variable light chain sequences prepared using sequences from murine mAb G1. G1-VK shows the original murine variable light chain sequence. AAZ0906 shows the acceptor human variable light chain sequence. Hu-G1_VK_v1 and Hu-G1_VK_v2 show two alternative versions of the humanized antibody variable light chain sequence, in which light chain CDR regions 1-3 of the human sequence are replaced with those of the murine light chain CDR regions 1-3.

FIG. 2 is a schematic showing proposed humanized variable heavy chain sequences prepared using sequences from murine mAb G1. G1-VH shows the original murine variable heavy chain sequence. AAC18323 shows the acceptor human variable heavy chain sequence. Hu-G1_VH_v1 and Hu-G1_VH_v2 show two alternative versions of the humanized antibody variable heavy chain sequence, in which heavy chain CDR regions 1-3 of the human sequence are replaced with those of the murine heavy chain CDR regions 1-3.

DETAILED DESCRIPTION

Figure 3:
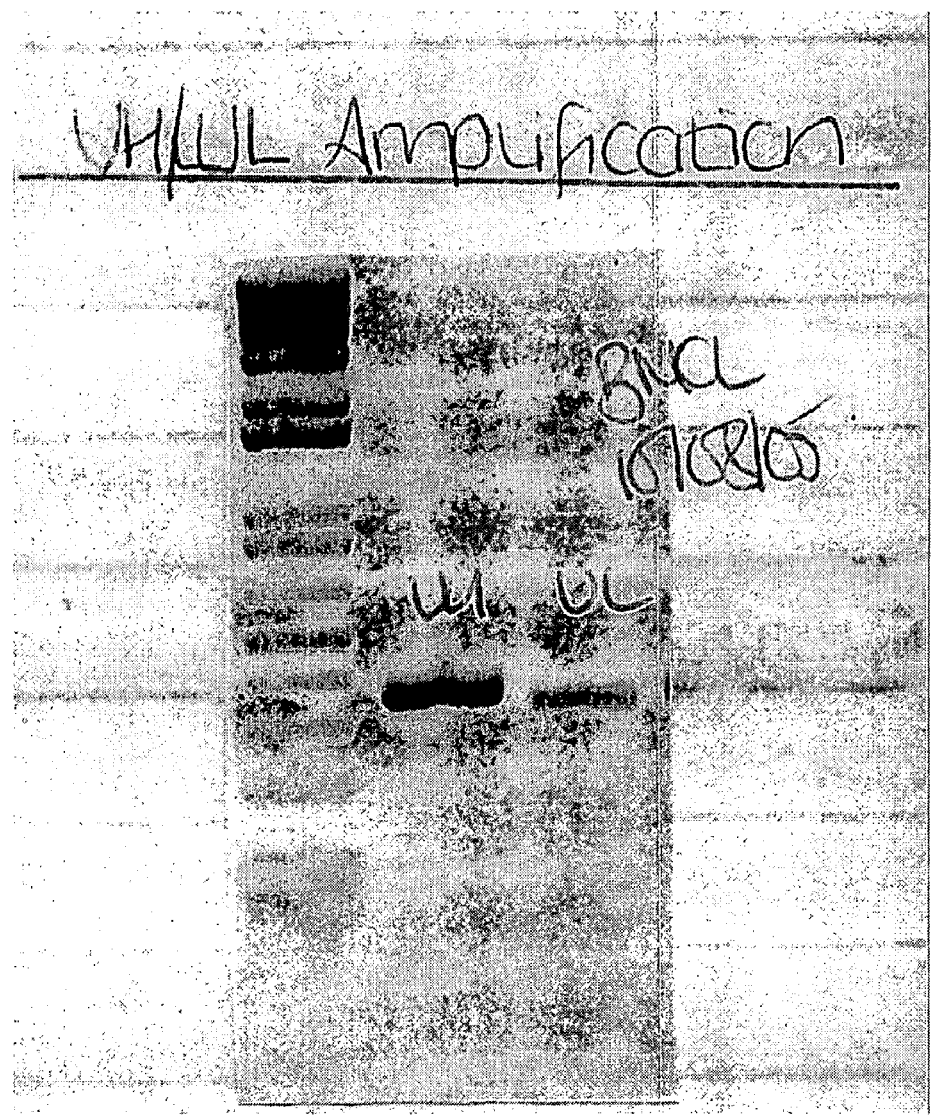
FIG. 3 is a photograph showing the purified variable light (VL) and variable heavy (VH) products that resulted following reverse transcriptase polymerase-chain reaction (RT-PCR) of RNA isolated from the hybridoma cells that express the murine mAb G1.

This invention provides compositions and methods for inhibiting inflammatory and thrombotic diseases and conditions mediated by P-selectin. Specifically, the invention provides chimeric or humanized immunoglobulins which have the ability to inhibit P-selectin-mediated adhesion of cells in vivo.

The immunoglobulins (or antibodies) of the invention selectively bind a functional epitope on P-selectin and can be used to prevent or reduce a disease condition associated with P-selectin activity, such as tissue injury and inflammation. Usually, binding of the antibodies to a functional epitope on P-selectin effectively inhibits adhesion of leukocytes to activated platelets and/or to the activated vascular endothelium in vivo. Antibodies demonstrating this property are referred to as "blocking" antibodies. Preferred blocking antibodies impair the adhesion of leukocytes to the activated vascular endothelium to prevent or inhibit an inflammatory and/or thrombotic condition.

The antibodies of the invention exhibit a specific binding affinity for P-selectin of at least $10^7$, $10^8$, $10^9$, or $10^{10}$ M$_{-1}$ or greater (e.g., up to, e.g., $10^{13}$ M$_{-1}$).

The production of non-human monoclonal antibodies, e.g., murine, lagomorpha, and equine, is well known and can be accomplished by, for example, immunizing an animal with a preparation containing cells bearing P-selectin (e.g., thrombin-activated platelets) or isolated P-selectin molecules or fragments thereof, such as extracellular domains. Antibody-producing cells obtained from the immunized animals are immortalized and screened, or screened first for the production of antibody which binds to P-selectin, and then immortalized. See, e.g., Harlow and Lane, Antibodies: A Laboratory Manual, Cold Spring Harbor Pubs., N.Y. (1988). Alternatively, substantially monospecific antibody populations can be produced by chromatographic purification of polyclonal sera.

Chimeric or humanized antibodies of the invention, which recognize P-selectin are provided. The invention provides humanized immunoglobulins having constant framework regions substantially from a human immunoglobulin (termed an acceptor immunoglobulin), as well as, in some instances, a majority of the variable region derived from a human immunoglobulin. The CDRs (all or a portion thereof, as well as discreet amino acids surrounding the CDRs) are provided from a non-human antibody, such as a mouse immunoglobulin (e.g., the light chain variable region CDRs set forth in SEQ ID NOs: 1-3 or the heavy chain variable region CDRs set forth in SEQ ID NOs: 4-6; which are derived from murine mAb G1 and referred to as the donor immunoglobulin). The constant region(s) of the immunoglobulin, may or may not be present. The chimeric or humanized antibodies of the present invention offer several advantages over the mouse donor antibody, which has already shown to be effective in animals models:

1) The human immune system should not recognize the framework or constant region of the humanized antibody as foreign, and therefore the antibody response against such an injected antibody should be less than against a totally foreign mouse antibody or a partially foreign chimeric antibody;

2) Because the effector portion of the humanized antibody is human, it may interact better with other parts of the human immune system; and 3) Injected mouse antibodies have been reported to have a half-life in the human circulation much shorter than the half-life of normal human antibodies (see, e.g., Shaw et al., J. Immunol. 138:4534-4538 (1987)). Injected humanized antibodies have a half-life essentially equivalent to naturally occurring human antibodies, allowing smaller and less frequent doses.

Cloning and Sequencing Variable Domains of Murine mAb G1

The cloning and sequencing of cDNA encoding the murine mAb G1 antibody heavy and light chain variable regions is described in Example 2, and the nucleotide and predicted amino acids sequences are shown in Table 2 below (i.e., SEQ ID NOs. 7-26).

Selection of Human Antibodies to Supply Framework Residues

The substitution of mouse CDRs into a human variable domain framework is most likely to result in retention of their correct spatial orientation if the human variable domain framework adopts the same or similar conformation to the mouse variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See, e.g., Kettleborough et al., Protein Engineering 4:773 (1991); Kolbinger et al., Protein Engineering 6:971 (1993).

Suitable human antibody sequences are identified by computer comparisons of the amino acid sequences of the mouse variable regions with the sequences of known human antibodies. The comparison is performed separately for heavy and light chains but the principles are similar for each.

Two human antibodies have been identified as suitable framework antibodies for producing the chimeric or humanized antibodies of the present invention. These include the human antibody sequence set forth in Genbank Accession No. AAZ09096 and the human antibody sequence set forth in Genbank Accession No. AAC18323. Genbank Accession No. AAZ09096 was identified using a homologous framework matching approach to correspond closely to the VL region of the murine mAb G1, while Genbank Accession No. AAC18323 was found to correspond closely to the VH region of the murine mAb G1. The chimeric or humanized antibodies of the invention are prepared by substituting all or a portion of the VL and VH regions of the human antibody sequences with the corresponding sequences from the murine mAb G1, or by substituting only the first, second, or third CDRs from the VL or VH domains.

Methods of preparing chimeric and humanized antibodies and antibody fragments are described in U.S. Pat. Nos. 4,816,567, 5,530,101, 5,622,701, 5,800,815, 5,874,540, 5,914,110, 5,928,904, 6,210,670, 6,677,436, and 7,067,313 and U.S. Patent Application Nos. 2002/0031508, 2004/0265311, and 2005/0226876. Preparation of antibody or fragments thereof is further described in U.S. Pat. Nos. 6,331,415, 6,818,216, and 7,067,313.

Computer Modeling

The unnatural juxtaposition of murine CDR regions with human variable framework region can result in unnatural conformational restraints, which, unless corrected by substitution of certain amino acid residues, lead to loss of binding affinity. The selection of amino acid residues for substitution is determined, in part, by computer modeling. Computer hardware and software for producing three-dimensional images of immunoglobulin molecules are widely available. In general, molecular models are produced starting from solved structures for immunoglobulin chains or domains thereof. The chains to be modeled are compared for amino acid sequence similarity with chains or domains of solved three dimensional structures, and the chains or domains showing the greatest sequence similarity is/are selected as starting points for construction of the molecular model. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits. Such a model can in turn serve as a starting point for predicting the three-dimensional structure of an antibody containing the murine mAb G1 complementarity determining regions substituted in human framework structures. Additional models can be constructed representing the structure when further amino acid substitutions to be discussed infra, are introduced.

Substitution of Amino Acid Residues

As noted above, the humanized antibodies of the invention comprise variable framework regions substantially from a human immunoglobulin and complementarity determining regions substantially from a mouse immunoglobulin termed murine mAb G1. Having identified the complementarity determining regions of murine mAb G1 (see, e.g., SEQ ID NOs: 1-3, which represent CDRs 1-3 of the VL region, and SEQ ID NOs: 4-6, which represent CDRs 1-3 of the VH region) and appropriate human acceptor immunoglobulins (as is discussed above), the next step is to determine which, if any, residues from these components should be substituted to optimize the properties of the resulting humanized antibody. In general, substitution of human amino acid residues with murine should be minimized, because introduction of murine residues increases the risk of the antibody eliciting a human anti-murine antibody (HAMA) response in humans. Amino acids are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

When an amino acid differs between a murine mAb G1 variable framework region and an equivalent human variable framework region, the human framework amino acid should usually be substituted by the equivalent mouse amino acid if it is reasonably expected that the amino acid:

(1) noncovalently binds antigen directly;

(2) is adjacent to a CDR region, is part of a CDR region under the alternative definition proposed by Kabat, Chothia, and others, or otherwise interacts with a CDR region (e.g., is within about 3 Å of a CDR region); or (3) participates in the $V_L$-$V_H$ interface.

Other candidates for substitution are acceptor human framework amino acids that are unusual for a human immunoglobulin at that position. These amino acids can be substituted with amino acids from the equivalent position of more typical human immunoglobulins. Alternatively, amino acids from equivalent positions in murine mAb G1 can be introduced into the human framework regions when such amino acids are typical of human immunoglobulin at the equivalent positions.

Usually the CDR regions in humanized antibodies are substantially identical, and more usually, identical to the corresponding CDR regions in the murine mAb G1 antibody. Although not usually desirable, it is sometimes possible to make one or more conservative amino acid substitutions of CDR residues without appreciably affecting the binding affinity of the resulting humanized immunoglobulin. Occasionally, substitution of CDR regions can result in enhanced binding affinity.

Other than for the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. However, in general, such substitutions are undesirable.

Production of Variable Regions

Having conceptually selected the CDR and framework components of humanized immunoglobulins, a variety of methods are available for producing such immunoglobulins. Because of the degeneracy of the code, a variety of nucleic acid sequences will encode each immunoglobulin amino acid sequence. The desired nucleic acid sequences can be produced by de novo solid-phase DNA synthesis or by PCR mutagenesis of an earlier prepared variant of the desired polynucleotide. Oligonucleotide-mediated mutagenesis is a preferred method for preparing substitution, deletion and insertion variants of target polypeptide DNA. See, e.g., Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

Selection of Constant Region

The variable segments of humanized antibodies produced as described supra are typically linked to at least a portion of an immunoglobulin constant region (Fc), typically that of a human immunoglobulin. Human constant region DNA sequences can be isolated in accordance with well-known procedures from a variety of human cells, but preferably immortalized B-cells (see, e.g., Kabat et al., supra, and WO87/02671) (each of which is incorporated by reference in its entirety for all purposes). Ordinarily, the antibody will contain both light chain and heavy chain constant regions. The heavy chain constant region usually includes CH1, hinge, CH2, CH3, and CH4 regions.

The humanized antibodies include antibodies having all types of constant regions, including IgM, IgG, IgD, IgA and IgE, and any isotype, including IgG1, IgG2, IgG3 and IgG4. When it is desired that the humanized antibody exhibit cytotoxic activity, the constant domain is usually a complement-fixing constant domain and the class is typically $IgG_1$. When such cytotoxic activity is not desirable, the constant domain may be of the $IgG_4$ class. The humanized antibody may comprise sequences from more than one class or isotype.

Expression Systems

Nucleic acids encoding humanized light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Such control sequences include a signal sequence, a promoter, an enhancer, and a transcription termination sequence. Expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362).

*E. coli* is one prokaryotic host useful particularly for cloning the polynucleotides of the present invention. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. *Saccharomyces* is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to express and produce the antibodies of the present invention (see, e.g., Winnacker, From Genes to Clones (VCH Publishers, N.Y., N.Y., 1987). Eukaryotic cells are actually preferred, because a number of suitable host cell lines capable of secreting intact immunoglobulins have been developed. Preferred suitable host cells for expressing nucleic acids encoding the immunoglobulins of the invention include: monkey kidney CV1 line transformed by SV40 (COS-7, ATCC CRL 1651); human embryonic kidney line (293) (Graham et al., J. Gen. Virol. 36:59 (1977)); baby hamster kidney cells (BHK, ATCC CCL 10); Chinese hamster ovary-cells-DHFR (CHO, Urlaub and Chasin, Proc. Natl. Acad. Sci. (USA) 77:4216 (1980)); mouse sertoli cells (TM4, Mather, Biol. Reprod. 23:243-251 (1980)); monkey kidney cells (CV1 ATCC CCL 70); african green monkey kidney cells (VERO-76, ATCC CRL 1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and, TRI cells (Mather, et al., Annals N.Y. Acad. Sci. 383:44-46 (1982)); and baculovirus cells.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts. (See generally Sambrook et al., Molecular Cloning: A Laboratory Manual (Cold Spring Harbor Press, 2nd ed., 1989) (incorporated by reference in its entirety for all purposes). When heavy and light chains are cloned on separate expression vectors, the vectors are cotransfected to obtain expression and assembly of intact immunoglobulins. After introduction of recombinant DNA, cell lines expressing immunoglobulin products are cell selected. Cell lines capable of stable expression are preferred (i.e., undiminished levels of expression after fifty passages of the cell line).

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (see generally Scopes, Protein Purification (Springer-Verlag, N.Y., 1982). Substantially pure immunoglobulins of at least about 90 to 95% homogeneity are preferred, and 98 to 99% or more homogeneity most preferred, for pharmaceutical uses.

The recombinant techniques described above can also be used for expression of native sequences encoding human or murine antibodies. This approach is particularly advantageous for expression of human antibodies that are isolated as unstable cell lines.

The intact antibodies and antibody fragments described herein are often produced by expression of nucleic acids. All nucleic acids encoding any antibody or antibody described in this application are expressly included in the invention. Modifications of nucleic acids are readily accomplished by a variety of well-known techniques, such as site-directed mutagenesis (see Gillman and Smith, Gene, 8:81-97 (1979) and Roberts, et al., Nature, 328:731-734 (1987)). Many of the nucleic acids of the invention show substantial sequence identity to nucleic acids encoding the heavy and light chains of murine mAb G1 or the exemplified humanized derivatives thereof.

Antibody Fragments

In another embodiment of the invention, fragments of the intact antibodies described herein are provided. Typically, these fragments compete with the intact antibody from which they were derived for specific binding to P-selectin, and bind with an affinity of at least $10^7$, $10^8$, $10^9$ $M_{-1}$, or $10^{10}$ $M_{-1}$. Antibody fragments include separate variable heavy chains, variable light chains, Fab, Fab', F(ab')$_2$, Fabc, and Fv. Fragments can be produced by enzymatic or chemical separation of intact immunoglobulins. For example, a F(ab')$_2$ fragment can be obtained from an IgG molecule by proteolytic digestion with pepsin at pH 3.0-3.5 using standard methods such as those described in Harlow and Lane, Antibodies: A Laboratory Manual, Cold Spring Harbor Pubs., N.Y. (1988). Fab fragments may be obtained from F(ab')$_2$ fragments by limited reduction, or from whole antibody by digestion with papain in the presence of reducing agents. (See id.) Fragments can also be produced by recombinant DNA techniques. Segments of nucleic acids encoding selected fragments are produced by digestion of full-length coding sequences with restriction enzymes, or by de novo synthesis. Often fragments are expressed in the form of phage-coat fusion proteins. This manner of expression is advantageous for affinity-sharpening of antibodies as discussed in Section IV.

Many of the immunoglobulins described herein can undergo non-critical amino-acid substitutions, additions or deletions in both the variable and constant regions without loss of binding specificity or effector functions, or intolerable reduction of binding affinity (i.e., below about $10^7$ $M_{-1}$). Usually, immunoglobulins incorporating such alterations exhibit substantial sequence identity to a reference immunoglobulin from which they were derived. Occasionally, a mutated immunoglobulin can be selected having the same specificity and increased affinity compared with a reference immunoglobulin from which it was derived. Phage-display technology offers powerful techniques for selecting such immunoglobulins. See, e.g., Dower et al., WO 91/17271 McCafferty et al., WO 92/01047; and Huse, WO 92/06204.

Therapeutic and Diagnostic Methods

The therapeutic methods employ the antibodies (whole and binding fragments) discussed herein as therapeutic agents for treatment of various inflammatory and thrombotic diseases, such as, e.g., sickle cell disease (or pain crisis associated with sickle cell disease), deep vein thrombosis, asthma, rheumatoid arthritis, psoriasis, and ischemia reperfusion injury. The antibodies can also be administered for prophylactic and therapeutic treatment of, e.g., transplant rejection, graft versus host disease, autoimmune diseases such as insulin-dependent diabetes mellitus, multiple sclerosis, stiff man syndrome, rheumatoid arthritis, myasthenia gravis and lupus erythematosus, and inflammatory disorders.

The therapeutic agents are particularly suitable for treatment of inflammatory and thrombotic conditions including post-ischemic leukocyte-mediated tissue damage (reperfusion injury) arising from traumatic shock, stroke, myocardial infarction, acute transplantation rejection, sickle cell disease (or pain crisis associated with sickle cell disease), frost-bite injury, compartment syndrome, and pathophysiologic conditions associated with cardio-pulmonary bypass, acute leukocyte-mediated lung injury (e.g., adult respiratory distress syndrome), septic shock, wound associated sepsis secondary to viral infection by e.g., herpes simplex virus, IgE-mediated allergic reactions such as acute phase asthmatic disease, and chronic inflammatory conditions, including rheumatoid arthritis, atopic dermatitis and psoriasis.

Ischemia/reperfusion injury is an inflammatory condition that occurs on restoring blood flow to organs suffering from an obstructed supply causing ischemia (oxygen deprivation). Unless rapidly relieved by reperfusion, ischemia causes death of surrounding cells, and eventually, death of a whole organ or patient. However, accumulating evidence suggests that reperfusion may itself exert deleterious effects on surrounding tissue. The deleterious effects of reperfusion are believed to result at least in part from an inflammatory response mediated by activated neutrophils in the restored blood flow. Some patients have whole-body ischemia, whereas in other patients ischemia is confined to particular parts or organs of the body.

For example, a patient may suffer from epidermal, myocardial, renal, cerebral, splenic, hepatic, spinal, splanchnic, pulmonary, partial-body, or whole-body ischemia. The therapeutic agents of the invention function by antagonizing the interaction of such leukocytes with P-selectin.

The P-selectin antibodies and pharmaceutical compositions thereof are particularly useful for parenteral administration, i.e., subcutaneously, intramuscularly or intravenously. A number of drug delivery approaches can be used.

For example, the P-selectin antibodies may be administered in liposomes, such as amphipaths, or dual character molecules (polar:nonpolar), which exist as aggregates in aqueous solution. Amphipaths include nonpolar lipids, polar lipids, mono- and diglycerides, sulfatides, lysolecithin, phospholipids, saponin, bile acids and salts. These molecules can exist as emulsions and foams, micelles, insoluble monolayers, liquid crystals, phospholipid dispersions and lamellar layers. These are generically referred to herein as liposomes. In these preparations, the drug to be delivered is incorporated as part of a liposome in which an anti-P-selectin immunoglobulin is embedded. In this embodiment, the immunoglobulin need not bind a functional epitope on the P-selectin molecule, so long as the immunoglobulin effectively targets the liposome to P-selectin molecules. When the liposomes are brought into proximity of the affected cells, they deliver the selected therapeutic compositions.

A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028, incorporated herein by reference. Targeting of liposomes using a variety of targeting agents (e.g., ligands, receptors and monoclonal antibodies) is well known in the art. (see, e.g., U.S. Pat. Nos. 4,957,773 and 4,603,044, both of which are incorporated herein by reference). Standard methods for coupling targeting agents to liposomes can be used. Antibody targeted liposomes can be constructed using, for instance, liposomes which incorporate protein A (see Renneisen, et al., J. Biol. Chem., 265:16337-16342 (1990) and Leonetti et al., Proc. Natl. Acad. Sci. (USA) 87:2448-2451 (1990).

Pharmaceutical compositions for parenteral administration usually comprise a solution of a therapeutic agent (e.g., an antibody against P-selectin) or a cocktail of several such agents dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH-adjusting and buffering agents, tonicity adjusting agents and the like, for example sodium acetate, sodium chloride, potassium chloride, calcium chloride, sodium lactate, etc. The concentration of antibody in these formulations can vary widely, i.e., from less than about 0.5%, usually at or at least about 0.1% to as much as 1.5% or 2.0% by weight and will be selected primarily based on fluid volumes, viscosities, etc., in accordance with the particular mode of administration selected. Actual methods for preparing parenterally administrable compositions will be known or apparent to those skilled in the art and are described in more detail in, for example, Remington's Pharmaceutical Sciences, 17th Ed., Mack Publishing Company, Easton, Pa. (1985), which is incorporated herein by reference.

The antibodies of this invention can be lyophilized for storage and reconstituted in a suitable carrier prior to use. This technique has been shown to be effective with conventional immunoglobulins and art-known lyophilization and reconstitution techniques can be employed. Lyophilization and reconstitution can lead to varying degrees of antibody activity loss (e.g., with conventional immunoglobulins, IgM antibodies tend to have greater activity loss than IgG antibodies) and that use levels may have to be adjusted to compensate.

The compositions containing the present antibodies or a cocktail thereof can be administered for the prophylactic and/or therapeutic treatments. In therapeutic application, compositions are administered to a patient in an amount sufficient to cure or at least partially arrest the disease condition (i.e., the inflammatory or thrombotic condition) and its complications. An amount adequate to accomplish this is defined as a "therapeutically effective dose." Amounts effective for this use will depend upon the severity of the disease and the general state of the patient's own immune system, but generally range from about 0.05 mg/kg body weight to about 5 mg/kg body weight, preferably between about 0.2 mg/kg body weight to about 1.5 mg/kg body weight.

Single or multiple administrations of the compositions can be carried out with dose levels and pattern being selected by the treating physician. In any event, the pharmaceutical formulations should provide a quantity of the immunoglobulins of this invention sufficient to treat the patient effectively.

The antibodies of invention (whole and binding fragments) can also be used for diagnostic purposes. An amount sufficient for these purposes is defined to be a "diagnostically effective dose." In diagnostic uses, the precise amounts will depend upon the patient's state of health, mode of administration, and the like. The antibodies may either be labeled or unlabeled. Unlabeled antibodies can be used in combination with other labeled antibodies (second antibodies) that are reactive with the antibody, such as antibodies specific for the particular immunoglobulin constant region. Alternatively, the antibodies can be directly labeled. A wide variety of labels may be employed, such as radionuclides, fluorescers, enzymes, enzyme substrates, enzyme cofactors, enzyme inhibitors, ligands (particularly haptens).

The antibodies (whole and binding fragments) are useful for detecting the presence of cells bearing P-selectin. The presence of such cells is diagnostic of an inflammatory condition or disease and may signal the need for commencement of a therapeutic method discussed supra. Diagnosis can be accomplished by removing a cellular sample from a patient. The amount of expressed P-selectin receptor in individual cells of the sample is then determined, e.g., by immunohistochemical staining of fixed cells or by Western blotting of a cell extract with an antibody of the invention.

The use of anti-P-selectin antibodies to treat inflammatory and thrombotic diseases is described in U.S. Pat. Nos. 5,622,701, 5,800,815, and 6,210,670 and U.S. Patent Application Nos. 2002/0031508, 2004/0265311 and 2005/0226876.

Diagnosis can also be achieved by in vivo administration of a labeled antibody (preferably a humanized or human antibody) and detection by in vivo imaging. The concentration of antibody administered should be sufficient that the binding to cells having the target antigen is detectable compared to the background signal. The diagnostic reagent can be labeled with a radioisotope for camera imaging, or a paramagnetic isotope for magnetic resonance or electron spin resonance imaging.

A change (typically an increase) in the level of P-selectin protein in a cellular sample or imaged from an individual, which is outside the range of clinically established normal levels, may indicate the presence of an undesirable disease condition in the individual from whom the sample was obtained, and/or indicate a predisposition of the individual for developing (or progressing through) such a disease condition.

Kits can also be supplied for use with the subject antibodies. Thus, the subject antibody composition of the present invention may be provided, usually in a lyophilized form in a container, either alone or in conjunction with other components necessary to treat or prevent a disease condition (e.g., instructions for use or other agents for use in treating the disease condition). The antibodies, which may be conjugated to a label or toxin, or unconjugated, are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to an anti-P-selectin antibody is employed in an assay, the second antibody will usually be present in a separate vial. The second antibody is typically conjugated to a label and formulated as described above.

The following examples are offered by way of illustration, not by limitation.

EXAMPLES

Example 1

Preparation of Chimeric or Humanized Antibodies of the Invention

Anti-P-selectin antibodies of the invention can be prepared by replacing one or more of the CDRs of a human antibody sequence with the CDRs from murine mAb G1. Alternatively, all or a part of the heavy and light chain variable regions from the murine mAb G1 can be used to replace the corresponding sequence in a human FR immunoglobulin. The light chain CDR sequences of the murine mAb G1 are set forth in SEQ ID NOs: 1-3, while the heavy chain CDR sequences of the murine mAb G1 are set forth in SEQ ID NOs: 4-6.

To design the Fv region of the humanized antibody which includes a light chain variable region VL and a heavy chain variable region VH, the human VL and VH sequences that are frequently expressed in the human body and that have a significant sequence identity with the mouse VL and VH sequences respectively are first identified. The human VL sequence indicated by Genbank Accession No. AAZ09096 and the human VH sequence indicated by Genbank Accession No. AAC18323 were selected on the basis of these two factors. Next, as is shown in FIGS. 1 and 2, the complementarity determining regions (CDRs) of the human VL and VH sequences were replaced by the corresponding CDRs of the anti-P-selectin mouse antibody: amino acids 24-34, 50-56, and 89-97 of SEQ ID NO:45 of the human VL ("AAZ09096") were substituted with amino acids 24-38, 54-60, and 93-101 of SEQ ID NO:44 of the mouse VL ("G1-VK") respectively yielding an "aggressively" humanized antibody VL ("Hu-G1-VK_v1") having the amino acid sequence SEQ ID NO:46; and amino acids 31-35, 50-66, and 99-111 of SEQ ID NO:49 of the human VH (the cleaved form of "AAC18323") were substituted with amino acids 31-35, 50-66, and 99-111 of SEQ ID NO:48 of the mouse VH ("G1-VH") respectively. Additional amino acids of the human VL and VH regions near the CDRs were substituted with corresponding amino acids present in the anti-P-selectin mouse antibody in order to better preserve the P-selectin binding affinity of the humanized antibodies. To identify residues proximal to the CDRs, the human sequences of the light chain ("AAZ09096") and the heavy chain ("AAC18323") were aligned to similar murine sequences 1IQW (a murine VL) and 1NMC (a murine VH) with known three-dimensional structures in the Protein Data Bank (PDB). By superimposing the human VL and VH sequences onto the murine VL and VH sequences and then energy minimizing the resulting structure using SPDBV software, amino acids in the human VL and VH proximal to the CDRs were identified: such proximal amino acids may be adjacent to the CDRs or positioned near the CDRs, e.g., within 4-6 Å of amino acids in a CDR, by virtue of the antibody's three-dimensional structure. Four amino acids of the human VL were identified as proximal to the CDRs, including amino acids 3, 4, 58, and 60 of SEQ ID NO:45 and ten amino acids of the human VH were identified as proximal to the CDRs, including amino acids 29, 38, 43, 48, 67, 68, 70, 72, 74, and 98 of SEQ ID NO:49, all of which differed between the respective mouse and human antibody sequences: substitution of the corresponding amino acids in the murine VL and VH were performed at many of these regions, depending on how "conservative" (having fewer human amino acids) or "aggressive" (having more human amino acids) the resulting humanized antibody was desired to be. In a more "conservative" version of the humanized antibody VL (having fewer human residues), amino acids 4 (methionine) and 58 (valine) of SEQ ID NO:45 of the human VL ("AAZ09096") were substituted with amino acids 4 (leucine) and 62 (isoleucine) of SEQ ID NO:44 of the mouse VL ("G1-VK") respectively yielding the "conservatively" humanized antibody VL ("Hu-G1-VK_v2") having the amino acid sequence SEQ ID NO:47. In an "aggressive" version of the humanized antibody VH (having more human amino acids), only amino acids 29 (leucine), 72 (glutamate), 74 (threonine), and 98 (threonine) of SEQ ID NO:49 of the human VH (the cleaved form of "AAC18323") were substituted with amino acids 29 (phenylalanine), 72 (valine), 74 (lysine), and 98 (arginine) of SEQ ID NO:48 of the mouse VH ("G1-VH") respectively, yielding the "aggressively" humanized antibody VH ("Hu-G1-VH_v1") having amino acid sequence SEQ ID NO:50. Similarly, in a "conservative" version of the humanized antibody VH, amino acids 29 (leucine), 48 (methionine), 67 (arginine), 68 (valine), 70 (methionine), 72 (glutamate), 74 (threonine), and 98 (threonine) of SEQ ID NO:49 of the human VH (the cleaved form of "AAC18323") were substituted with amino acids 29 (phenylalanine), 48 (isoleucine), 67 (lysine), 68 (alanine), 70 (leucine), 72 (valine), 74 (lysine), and 98 (arginine) of SEQ ID NO:48 of the mouse VH ("G1-VH") respectively, yielding the "conservatively" humanized antibody VH ("Hu-G1-VH_v2") having amino acid sequence SEQ ID NO:51. Using this procedure, any anti-P-selectin humanized or chimeric antibody, antibody fragment, bifunctional antibody, or antibody derivative having a variable Fv region with CDRs having, e.g., 90%, 95%, 99%, or more sequence identity to amino acids 24-38, 54-60, or 93-101 of SEQ ID NO:44 of the mouse VL ("G1-VK") or amino acids 31-35, 50-66, or 99-111 of SEQ ID NO:48 of the mouse VH ("G1-VH"), which binds P-selectin, may be designed and synthesized using techniques known in the art. Preferably, any anti-P-selectin humanized or chimeric antibody, antibody fragment, bifunctional antibody, or antibody derivative will have valine at the $3^{rd}$ position, leucine at the $4^{th}$ position, isoleucine at the $58^{th}$ position, or alanine at the $60^{th}$ position of one or more of its VL regions or a phenylalanine at the $29^{th}$ position, lysine at the $38^{th}$ position, glutamine at the 43$^{rd}$ position, isoleucine at the 48$^{th}$ position, lysine at the 67$^{th}$ position, alanine at the 68$^{th}$ position, leucine at the 70$^{th}$ position, valine at the 72$^{nd}$ position, lysine at the 74$^{th}$ position, or arginine at the 98$^{th}$ position of one or more of its VH regions.

Example 2

Cloning of Murine Antibody mRNA was extracted from the hybridoma cell pellets, and agarose gel analysis showed a high yield of the extracted RNA from the pellet. cDNA was created from the RNA by reverse-transcription with an oligo(dT) primer. PCR reactions using variable domain degenerate primers to amplify the VH and VL regions of the monoclonal antibody DNA gave the bands shown in FIG. 3. The purified VH and VL PCR products from RT-PCR were cloned into a sequencing vector and positive transformants were determined by colony PCR. From the RT-PCR, 6 VL and 6 VH clones were identified and the DNA was sequenced. The amino acid sequence was derived from the sequence of the DNA open reading frame. There was a single consensus sequence for both the variable light chain and the variable heavy chain (see Tables 1 and 2).

TABLE 1

CDR sequences from murine mAb G1

Amino Acid Sequences

| | |
|---|---|
| VL CDR1: | KASQSVDYDGHSYMN (SEQ ID NO: 1) |
| VL CDR2: | AASNLES (SEQ ID NO: 2) |
| VL CDR3: | QQSDENPLT. (SEQ ID NO: 3) |
| VH CDR1: | SYDIN (SEQ ID NO: 4) |
| VH CDR2: | WIYPGDGSIKYNEKFKG (SEQ ID NO: 5) |
| VH CDR3: | RGEYGNYEGAMDY (SEQ ID NO: 6) |

TABLE 2

VL and VH Sequences from cloned RT-PCR products from hybridoma cells expressing murine mAb G1. 6 VL clones were identified and sequenced and 6 VH clones were identified and sequenced.

Clone VL 1

DNA sequence (SEQ ID NO: 7):
GACATTGTGCTAACCCAATCTCCAGCTTCTTTGGCTGTGTCTCTAGGGCAG

AGGGCCACCATCTCCTGCAAGGCCAGCCAAAGTGTTGATTATGATGGTCA

TAGTTATATGAACTGGTACCAACAGAAACCAGGACAGCCACCCAAACTCC

TCATCTATGCTGCATCCAATCTAGAATCTGGGATCCCAGCCAGGTTTAGTG

GCAGTGGGTCTGGGACAGACTTCACCCTCAACATCCATCCTGTGGAGGAG

GAGGATGCTGCAACCTATTACTGTCAGCAAAGTGATGAAAATCCCCTCAC

GTTCGGTACTGGGACCAAGCTGGAGCTGAAACGG

Amino acid sequence (SEQ ID NO: 8):
DIVLTQSPASLAVSLGQRATISCKASQSVDYDGHSYMNWYQQKPGQPPKL

LIYAASNLESGIPARFSGSGSGTDFTLNIHPVEEEDAATYYCQQSDENPL

TFGTGTKLELKR

TABLE 2-continued

VL and VH Sequences from cloned RT-PCR products from hybridoma cells expressing murine mAb G1. 6 VL clones were identified and sequenced and 6 VH clones were identified and sequenced.

Clone VL2

DNA sequence (SEQ ID NO: 9):
GACATTGTGCTGACCCAATCTCCAGCTTCTTTGGCTGTGTCTCTAGGGCAG

AGGGCCACCATCTCCTGCAAGGCCAGCCAAAGTGTTGATTATGATGGTCA

TAGTTATATGAACTGGTACCAACAGAAACCAGGACAGCCACCCAAACTCC

TCATCTATGCTGCATCCAATCTAGAATCTGGGATCCCAGCCAGGTTTAGTG

GCAGTGGGTCTGGGACAGACTTCACCCTCAACATCCATCCTGTGGAGGAG

GAGGATGCTGCAACCTATTACTGTCAGCAAAGTGATGAAAATCCCCTCAC

GTTCGGTACTGGGACCAAGCTGGAGCTGAAACGG

Amino acid sequence (SEQ ID NO: 10):
DIVLTQSPASLAVSLGQRATISCKASQSVDYDGHSYMNWYQQKPGQPPK

LLIYAASNLESGIPARFSGSGSGTDFTLNIHPVEEEDAATYYCQQSDEN

PLTFGTGTKLELKR

Clone VL3

DNA sequence (SEQ ID NO: 11):
GACATCCAGATGACACAGTCTCCAGCTTCTTTGGCTGTGTCTCTAGGGCAG

AGGGCCACCATCTCCTGCAAGGCCAGCCAAAGTGTTGATTATGATGGTCA

TAGTTATATGAACTGGTACCAACAGAAACCAGGACAGCCACCCAAACTCC

TCATCTATGCTGCATCCAATCTAGAATCTGGGATCCCAGCCAGGTTTAGTG

GCAGTGGGTCTGGGACAGACTTCACCCTCAACATCCATCCTGTGGAGGAG

GAGGATGCTGCAACCTATTACTGTCAGCAAAGTGATGAAAATCCCCTCAC

GTTCGGTACTGGGACCAAGCTGGAGCTGAAACGG

Amino acid sequence (SEQ ID NO: 12):
DIQMTQSPASLAVSLGQRATISCKASQSVDYDGHSYMNWYQQKPGQPPKL

LIYAASNLESGIPARFSGSGSGTDFTLNIHPVEEEDAATYYCQQSDENPL

TFGTGTKLELKR

Clone VL4

DNA sequence (SEQ ID NO: 13):
GACATTGTGCTGACCCAGTCTCCAGCTTCTTTGGCTGTGTCTCTAGGGCAG

AGGGCCACCATCTCCTGCAAGGCCAGCCAAAGTGTTGATTATGATGGTCA

TAGTTATATGAACTGGTACCAACAGAAACCAGGACAGCCACCCAAACTCC

TCATCTATGCTGCATCCAATCTAGAATCTGGGATCCCAGCCAGGTTTAGTG

GCAGTGGGTCTGGGACAGACTTCACCCTCAACATCCATCCTGTGGAGGAG

GAGGATGCTGCAACCTATTACTGTCAGCAAAGTGATGAAAATCCCCTCAC

GTTCGGTACTGGGACCAAGCTGGAGCTGA

Amino acid sequence (SEQ ID NO: 14):
DIVLTQSPASLAVSLGQRATISCKASQSVDYDGHSYMNWYQQKPGQPPK

LLIYAASNLESGIPARFSGSGSGTDFTLNIHPVEEEDAATYYCQQSDEN

PLTFGTGTKLEL

TABLE 2-continued

VL and VH Sequences from cloned RT-PCR products
from hybridoma cells expressing murine mAb G1.
6 VL clones were identified and sequenced and
6 VH clones were identified and sequenced.

Clone VL6

DNA sequence (SEQ ID NO: 15):
GACATTGTGCTAACCCAGTCTCCAGCTTCTTTGGCTGTGTCTCTAGGGCAG

AGGGCCACCATCTCCTGCAAGGCCAGCCAAAGTGTTGATTATGATGGTCA

TAGTTATATGAACTGGTACCAACAGAAACCAGGACAGCCACCCAAACTCC

TCATCTATGCTGCATCCAATCTAGAATCTGGGATCCCAGCCAGGTTTAGTG

GCAGTGGGTCTGGGACAGACTTCACCCTCAACATCCATCCTGTGGAGGAG

GAGGATGCTGCAACCTATTACTGTCAGCAAAGTGATGAAAATCCCCTCAC

GTTCGGTACTGGGACCAAGCTGGAGCTGAAACGG

Amino acid sequence (SEQ ID NO: 16):
DIVLTQSPASLAVSLGQRATISCKASQSVDYDGHSYMNWYQQKPGQPPK

LLIYAASNLESGIPARFSGSGSGTDFTLNIHPVEEEDAATYYCQQSDEN

PLTFGTGTKLELKR

Clone VH2

DNA sequence (SEQ ID NO: 17):
AGGTGAAGCTGCAGCAGTCAGGACCTGAGCTGGTGAAGCCTGGGGCTTTA

GTGAAGATATCCTGCAAGGCTTCTGGTTACACCTTCACAAGCTACGATATA

AATTGGGTGAAGCAGAGGCCTGGACAGGGACTTGAGTGGATTGGATGGAT

TTATCCTGGAGATGGTAGTATTAAGTACAATGAGAAATTCAAGGGCAAGG

CCACACTGACTGTAGACAAATCCTCCAGCACAGCCTACATGCAGGTCAGC

AGCCTGACTTCTGAGAATTCTGCAGTCTATTTCTGTGCAAGACGGGGGA

GTATGGTAACTACGAGGGGCTATGGACTACTGGGGCCAAGGGACCACGG

TCACCGTCTCCTCA

Amino acid sequence (SEQ ID NO: 18):
VKLQQSGPELVKPGALVKISCKASGYTFTSYDINWVKQRPGQGLEWIGW

IYPGDGSIKYNEKFKGKATLTVDKSSSTAYMQVSSLTSENSAVYFCARR

GEYGNYEGAMDYWGQGTTVTVSS

Clone VH3

DNA sequence (SEQ ID NO: 19):
AGGTCAAGCTGCAGCAGTCTGGACCTGAGCTGGTGAAGCCTGGGGCTTTA

GTGAAGATATCCTGCAAGGCTTCTGGTTACACCTTCACAAGCTACGATATA

AATTGGGTGAAGCAGAGGCCTGGACAGGGACTTGAGTGGATTGGATGGAT

TTATCCTGGAGATGGTAGTATTAAGTACAATGAGAAATTCAAGGGCAAGG

CCACACTGACTGTAGACAAATCCTCCAGCACAGCCTACATGCAGGTCAGC

AGCCTGACTTCTGAGAATTCTGCAGTCTATTTCTGTGCAAGACGGGGGA

GTATGGTAACTACGAGGGGCTATGGACTACTGGGGCCAAGGGACCACGG

TCACCGTCTCCTCA

Amino acid sequence (SEQ ID NO: 20):
VKLQQSGPELVKPGALVKISCKASGYTFTSYDINWVKQRPGQGLEWIGW

IYPGDGSIKYNEKFKGKATLTVDKSSSTAYMQVSSLTSENSAVYFCARR

GEYGNYEGAMDYWGQGTTVTVSS

TABLE 2-continued

VL and VH Sequences from cloned RT-PCR products
from hybridoma cells expressing murine mAb G1.
6 VL clones were identified and sequenced and
6 VH clones were identified and sequenced.

Clone VH4

DNA sequence (SEQ ID NO: 21):
AGGTGCAGCTGCAGGAGTCTGGACCTGAGCTGGTGAAGCCTGGGCTTTA

GTGAAGATATCCTGCAAGGCTTCTGGTTACACCTTCACAAGCTACGATATA

AATTGGGTGAAGCAGAGGCCTGGACAGGGACTTGAGTGGATTGGATGGAT

TTATCCTGGAGATGGTAGTATTAAGTACAATGAGAAATTCAAGGGCAAGG

CCACACTGACTGTAGACAAATCCTCCAGCACAGCCTACATGCAGGTCAGC

AGCCTGACTTCTGAGAATTCTGCAGTCTATTTCTGTGCAAGACGGGGGA

GTATGGTAACTACGAGGGGCTATGGACTACTGGGGCCAAGGGACCACGG

TCACCGTCTCCTCA

Amino acid sequence (SEQ ID NO: 22):
VQLQESGPELVKPGALVKISCKASGYTFTSYDINWVKQRPGQGLEWIGW

IYPGDGSIKYNEKFKGKATLTVDKSSSTAYMQVSSLTSENSAVYFCARR

GEYGNYEGAMDYWGQGTTVTVSS

Clone VH5

DNA sequence (SEQ ID NO: 23):
AGGTGAAGCTGCAGCAGTCTGGACCTGAGCTGGTGAAGCCTGGGGCTTTA

GTGAAGATATCCTGCAAGGCTTCTGGTTACACCTTCACAAGCTACGATATA

AATTGGGTGAAGCAGAGGCCTGGACAGGGACTTGAGTGGATTGGATGGAT

TTATCCTGGAGATGGTAGTATTAAGTACAATGAGAAATTCAAGGGCAAGG

CCACACTGACTGTAGACAAATCCTCCAGCACAGCCTACATGCAGGTCAGC

AGCCTGACTTCTGAGAATTCTGCAGTCTATTTCTGTGCAAGACGGGGGA

GTATGGTAACTACGAGGGGCTATGGACTACTGGGGCCAAGGGACCACGG

TCACCGTCTCCTCA

Amino acid sequence (SEQ ID NO: 24):
VKLQQSGPELVKPGALVKISCKASGYTFTSYDINWVKQRPGQGLEWIG

WIYPGDGSIKYNEKFKGKATLTVDKSSSTAYMQVSSLTSENSAVYFCA

RRGEYGNYEGAMDYWGQGTTVTVSS

Clone VH6

DNA sequence (SEQ ID NO: 25):
AGGTGCAGCTGCAGCAGTCAGGACCTGAACTGGTGAAGCCTGGGGCTTTA

GTGAAGATATCCTGCAAGGCTTCTGGTTACACCTTCACAAGCTACGATATA

AATTGGGTGAAGCAGAGGCCTGGACAGGGACTTGAGTGGATTGGATGGAT

TTATCCTGGAGATGGTAGTATTAAGTACAATGAGAAATTCAAGGGCAAGG

CCACACTGACTGTAGACAAATCCTCCAGCACAGCCTACATGCAGGTCAGC

AGCCTGACTTCTGAGAATTCTGCAGTCTATTTCTGTGCAAGACGGGGGA

GTATGGTAACTACGAGGGGCTATGGACTACTGGGGCCAAGGGACCACGG

TCACCGTCTCCTCA

TABLE 2-continued

VL and VH Sequences from cloned RT-PCR products
from hybridoma cells expressing murine mAb G1.
6 VL clones were identified and sequenced and
6 VH clones were identified and sequenced.

Amino acid sequence (SEQ ID NO: 26):
VQLQQSGPELVKPGALVKISCKASGYTFTSYDINWVKQRPGQGLEWIGW

IYPGDGSIKYNEKFKGKATLTVDKSSSTAYMQVSSLTSENSAVYFCARR

GEYGNYEGAMDYWGQGTTVTVSS

Consensus Sequences from the Murine mAb VL and VH Clones Sequenced:

Light chain variable domain:
DNA sequence (SEQ ID NO: 27):
GACATTGTGCTGACCCAGTCTCCAGCTTCTTTGGCTGTGTCTCTAGGGCAG

AGGGCCACCATCTCCTGCAAGGCCAGCCAAAGTGTTGATTATGATGGTCA

TAGTTATATGAACTGGTACCAACAGAAACCAGGACAGCCACCCAAACTCC

TCATCTATGCTGCATCCAATCTAGAATCTGGGATCCCAGCCAGGTTTAGTG

GCAGTGGGTCTGGGACAGACTTCACCCTCAACATCCATCCTGTGGAGGAG

GAGGATGCTGCAACCTATTACTGTCAGCAAAGTGATGAAAATCCCCTCAC

GTTCGGTACTGGGACCAAGCTGGAGCTGAAACGG

Amino acid sequence (SEQ ID NO: 28):
DIVLTQSPASLAVSLGQRATISCKASQSVDYDGHSYMNWYQQKPGQPPKLL

IYAASNLESGIPARFSGSGSGTDFTLNIHPVEEEDAATYYCQQSDENPLTF

GTGTKLELKR

Heavy chain variable domain:
DNA sequence (SEQ ID NO: 29): *
AGGTGAAGCTGCAGCAGTCTGGACCTGAGCTGGTGAAGCCTGGGCTTTA

GTGAAGATATCCTGCAAGGCTTCTGGTTACACCTTCACAAGCTACGATATA

AATTGGGTGAAGCAGAGGCCTGGACAGGGACTTGAGTGGATTGGATGGAT

TTATCCTGGAGATGGTAGTATTAAGTACAATGAGAAATTCAAGGGCAAGG

CCACACTGACTGTAGACAAATCCTCCAGCACAGCCTACATGCAGGTCAGC

AGCCTGACTTCTGAGAATTCTGCAGTCTATTTCTGTGCAAGACGGGGGA

GTATGGTAACTACGAGGGGCTATGGACTACTGGGGCCAAGGGACCACGG

TCACCGTCTCCTCA

Amino acid sequence (SEQ ID NO: 30):*
VKLQQSGPELVKPGALVKISCKASGYTFTSYDINWVKQRPGQGLEWIGW

IYPGDGSIKYNEKFKGKATLTVDKSSSTAYMQVSSLTSENSAVYFCARR

GEYGNYEGAMDYWGQGTTVTVSS
* The K in position 2 of this sequence does not
match the information from directN-terminal
protein sequencing of the antibody. That sequencing
determined that a Q residue is present in that
position; a Q residue is also present in the
translation of cDNA clones VH4 and VH6 of this
report. Therefore, the DNA/translated protein
sequences of clones VH4 and VH6 should be regarded
as the correct sequence of the heavy chain:

DNA sequence (SEQ ID NO: 31):
AGGTGCAGCTGCAGCAGTCAGGACCTGAACTGGTGAAGCCTGGGCTTTA

GTGAAGATATCCTGCAAGGCTTCTGGTTACACCTTCACAAGCTACGATATA

-continued
AATTGGGTGAAGCAGAGGCCTGGACAGGGACTTGAGTGGATTGGATGGAT

TTATCCTGGAGATGGTAGTATTAAGTACAATGAGAAATTCAAGGGCAAGG

CCACACTGACTGTAGACAAATCCTCCAGCACAGCCTACATGCAGGTCAGC

AGCCTGACTTCTGAGAATTCTGCAGTCTATTTCTGTGCAAGACGGGGGA

GTATGGTAACTACGAGGGGCTATGGACTACTGGGGCCAAGGGACCACGG

TCACCGTCTCCTCA

Amino acid sequence (SEQ ID NO: 32):
VQLQQSGPELVKPGALVKISCKASGYTFTSYDINWVKQRPGQGLEWIGW

IYPGDGSIKYNEKFKGKATLTVDKSSSTAYMQVSSLTSENSAVYFCARR

GEYGNYEGAMDYWGQGTTVTVSS

In addition, according to comparison with other antibody sequences, there is likely one more amino acid residue N-terminal to the V residue in the heavy chain. This is supported by the fact that the N-terminus of the heavy-chain had to be "unblocked" prior to direct protein N-terminal sequencing. Sequence comparisons with other antibodies suggest that the missing residue is a Q. Thus, the sequence of the VH would be:

(SEQ ID NO: 33)
QVQLQQSGPELVKPGALVKISCKASGYTFTSYDINWVKQRPGQGLEWI

GWIYPGDGSIKYNEKFKGKATLTVDKSSSTAYMQVSSLTSENSAVYFC

ARRGEYGNYEGAMDYWGQGTTVTVSS

G1 N-Terminal Amino Acid Sequence

Light: Sequencing is taking place at an initial difference level of about 750 pmol. The sequence is: D I V L T Q S P A S L A V S L G Q R A T I S S (?) K A (SEQ ID NO: 34)

Heavy: Sequencing is taking place at an initial difference level of about 165 pmol. The sequence is. V Q L Q Q S G P E L V K P GAL V K I S 0 K A S G (SEQ ID NO: 35)

Example 3

Sequences for the Humanized P-Selectin Immunoglobulin Based on G1

Nucleotide Sequences for Hu-G1

V1 and V2 (shown below) refer to the "aggressive" (i.e., more human) and "conservative" (i.e., more murine) versions of the humanized antibody amino acid sequences, respectively. For each of those, the "A" codons were generated by starting with those of the human framework sequences and the codons of the mouse CDR sequences, then changing codons as needed to match the actual humanized amino acid sequence. The "B" codons started with the mouse codons and then changed where needed to match the humanized amino acid sequences.

| Chain | V1-aggressive (No. mouse frm.) | V2-conservative (No. mouse frm.) |
|---|---|---|
| VK | 0 | 2 |
| VH | 4 | 8 |

Light chain:

Hu-G1-VK_v1_nuc-A

```
  1 D   I   Q   M   T   Q   S   P   S   S   L   S   A   S   V   G   D   R   V   T
  1 GACATCCAGATGACCCAGTCTCCATCCTCCCTGTCTGCATCTGTAGGAGACAGAGTCACC
 21 I   T   C   K   A   S   Q   S   V   D   Y   D   G   H   S   Y   M   N   W   Y
 61 ATCACTTGCAAGGCCAGCAGAGCGTTGATTATGATGGTCATAGTTATATGAACTGGTAT
 41 Q   Q   K   P   G   K   A   P   K   L   L   I   Y   A   A   S   N   L   E   S
121 CAGCAGAAACCAGGGAAAGCCCCTAAGCTCCTGATCTATGCTGCATCCAATTTGGAATCT
 61 G   V   P   S   R   F   S   G   S   G   S   G   T   D   F   T   L   T   I   S
181 GGGGTCCCATCAAGGTTCAGTGGCAGTGGATCTGGGACAGATTTCACTCTCACCATCAGC
 81 S   L   Q   P   E   D   F   A   T   Y   Y   C   Q   Q   S   D   E   N   P   L
241 AGTCTGCAACCTGAAGATTTTGCAACTTACTACTGTCAGCAAAGTGATGAAAATCCCCTC
101 T   F   G   G   G   T   K   V   E   I   K              (SEQ ID NO: 36)
301 ACTTTCGGCGGAGGGACCAAGGTGGAGATCAAA                      (SEQ ID NO: 52)
```

Hu-G1-VK_v1_nuc-B

```
  1 D   I   Q   M   T   Q   S   P   S   S   L   S   A   S   V   G   D   R   V   T
  1 GACATTCAGATGACCCAGTCTCCATCCTCTTTGTCTGCATCTGTAGGGGACAGGGTCACC
 21 I   T   C   K   A   S   Q   S   V   D   Y   D   G   H   S   Y   M   N   W   Y
 61 ATCACTTGCAAGGCCAGCCAGAGCGTTGATTATGATGGTCATAGTTATATGAACTGGTAC
 41 Q   Q   K   P   G   K   A   P   K   L   L   I   Y   A   A   S   N   L   E   S
121 CAACAGAAACCAGGAAAAGCCCCCAAACTCCTGATCTATGCTGCATCCAATTTGGAATCT
 61 G   V   P   S   R   F   S   G   S   G   S   G   T   D   F   T   L   T   I   S
181 GGGGTCCCATCAAGGTTTAGTGGCAGTGGGTCTGGGACAGACTTCACCCTCACCATCAGC
 81 S   L   Q   P   E   D   F   A   T   Y   Y   C   Q   Q   S   D   E   N   P   L
241 AGTCTGCAACCTGAGGATTTTGCAACCTATTACTGTCAGCAAAGTGATGAAAATCCCCTC
101 T   F   G   G   G   T   K   V   E   I   K              (SEQ ID NO: 37)
301 ACTTTCGGTGGAGGGACCAAGGTGGAGATCAAA                      (SEQ ID NO: 53)
```

Hu-G1-VK_v2_nuc-A

```
  1 D   I   Q   L   T   Q   S   P   S   S   L   S   A   S   V   G   D   R   V   T
  1 GACATCCAGCTGACCCAGTCTCCATCCTCCCTGTCTGCATCTGTAGGAGACAGAGTCACC
 21 I   T   C   K   A   S   Q   S   V   D   Y   D   G   H   S   Y   M   N   W   Y
 61 ATCACTTGCAAGGCCAGCCAGAGCGTTGATTATGATGGTCATAGTTATATGAACTGGTAT
 41 Q   Q   K   P   G   K   A   P   K   L   L   I   Y   A   A   S   N   L   E   S
121 CAGCAGAAACCAGGGAAAGCCCCTAAGCTCCTGATCTATGCTGCATCCAATTTGGAATCT
 61 G   I   P   S   R   F   S   G   S   G   S   G   T   D   F   T   L   T   I   S
181 GGGATCCCATCAAGGTTCAGTGGCAGTGGATCTGGGACAGATTTCACTCTCACCATCAGC
 81 S   L   Q   P   E   D   F   A   T   Y   Y   C   Q   Q   S   D   E   N   P   L
241 AGTCTGCAACCTGAAGATTTTGCAACTTACTACTGTCAGCAAAGTGATGAAAATCCCCTC
101 T   F   G   G   G   T   K   V   E   I   K              (SEQ ID NO: 38)
301 ACTTTCGGCGGAGGGACCAAGGTGGAGATCAAA                      (SEQ ID NO: 54)
```

Hu-G1-VK_v2_nuc-B

```
  1 D   I   Q   L   T   Q   S   P   S   S   L   S   A   S   V   G   D   R   V   T
  1 GACATTCAGCTGACCCAGTCTCCATCCTCTTTGTCTGCATCTGTAGGGGACAGGGTCACC
 21 I   T   C   K   A   S   Q   S   V   D   Y   D   G   H   S   Y   M   N   W   Y
 61 ATCACTTGCAAGGCCAGCCAGAGCGTTGATTATGATGGTCATAGTTATATGAACTGGTAC
 41 Q   Q   K   P   G   K   A   P   K   L   L   I   Y   A   A   S   N   L   E   S
121 CAACAGAAACCAGGAAAAGCCCCCAAACTCCTGATCTATGCTGCATCCAATTTGGAATCT
 61 G   I   P   S   R   F   S   G   S   G   S   G   T   D   F   T   L   T   I   S
181 GGGATCCCATCAAGGTTTAGTGGCAGTGGGTCTGGGACAGACTTCACCCTCACCATCAGC
 81 S   L   Q   P   E   D   F   A   T   Y   Y   C   Q   Q   S   D   E   N   P   L
241 AGTCTGCAACCTGAGGATTTTGCAACCTATTACTGTCAGCAAAGTGATGAAAATCCCCTC
101 T   F   G   G   G   T   K   V   E   I   K              (SEQ ID NO: 39)
301 ACTTTCGGTGGAGGGACCAAGGTGGAGATCAAA                      (SEQ ID NO: 55)
```

-continued

Heavy chain:

Hu-G1-VH_v1_nuc-A

```
  1 Q V Q L V Q S G A E V K K P G A S V K V
  1 CAGGTCCAGCTGGTACAGTCTGGGGCTGAGGTGAAGAAGCCTGGGGCCTCAGTGAAGGTC
 21 S C K V S G Y T F T S Y D I N W V R Q A
 61 TCCTGCAAGGTTTCCGGATACACCTTCACTAGCTACGATATAAATTGGGTGCGACAGGCT
 41 P G K G L E W M G W I Y P G D G S I K Y
121 CCTGGAAAAGGGCTTGAGTGGATGGGATGGATTTATCCTGGAGATGGTAGCATTAAGTAC
 61 N E K F K G R V T M T V D K S T D T A Y
181 AATGAGAAATTCAAGGGCAGAGTCACCATGACCGTAGACAAATCTACAGACACAGCCTAC
 81 M E L S S L R S E D T A V Y Y C A R R G
241 ATGGAGCTGAGCAGCCTGAGATCTGAGGACACAGCCGTGTATTACTGTGCAAGACGGGGG
101 E Y G N Y E G A M D Y W G Q G T L V T V
301 GAGTATGGTAACTACGAGGGGGCTATGGACTACTGGGGCCAGGGAACCCTGGTCACCGTC
121 S S           (SEQ ID NO: 40)
361 TCCTCA        (SEQ ID NO: 56)
```

Hu-G1-VH_v1_nuc-B

```
  1 Q V Q L V Q S G A E V K K P G A S V K V
  1 CAGGTGCAGCTGGTACAGTCAGGAGCTGAAGTGAAGAAGCCTGGGGCTTCAGTGAAGGTC
 21 S C K V S G Y T F T S Y D I N W V R Q A
 61 TCCTGCAAGGTTTCTGGTTACACCTTCACAAGCTACGATATAAATTGGGTGCGACAGGCT
 41 P G K G L E W M G W I Y P G D G S I K Y
121 CCTGGAAAAGGACTTGAGTGGATGGGATGGATTTATCCTGGAGATGGTAGCATTAAGTAC
 61 N E K F K G R V T M T V D K S T D T A Y
181 AATGAGAAATTCAAGGGCAGAGTCACAATGACTGTAGACAAATCCACAGACACAGCCTAC
 81 M E L S S L R S E D T A V Y Y C A R R G
241 ATGGAGCTGAGCAGCCTGAGATCTGAGGACACAGCAGTCTATTACTGTGCAAGACGGGGG
101 E Y G N Y E G A M D Y W G Q G T L V T V
301 GAGTATGGTAACTACGAGGGGGCTATGGACTACTGGGGCCAAGGGACCCTGGTCACCGTC
121 S S           (SEQ ID NO: 41)
361 TCCTCA        (SEQ ID NO: 57)
```

Hu-G1-VH_v2_nuc-A

```
  1 Q V Q L V Q S G A E V K K P G A S V K V
  1 CAGGTCCAGCTGGTACAGTCTGGGGCTGAGGTGAAGAAGCCTGGGGCCTCAGTGAAGGTC
 21 S C K V S G Y T F T S Y D I N W V R Q A
 61 TCCTGCAAGGTTTCCGGATACACCTTCACTAGCTACGATATAAATTGGGTGCGACAGGCT
 41 P G K G L E W I G W I Y P G D G S I K Y
121 CCTGGAAAAGGGCTTGAGTGGATTGGATGGATTTATCCTGGAGATGGTAGCATTAAGTAC
 61 N E K F K G K A T L T V D K S T D T A Y
181 AATGAGAAATTCAAGGGCAAGGCCACCCTGACCGTAGACAAATCTACAGACACAGCCTAC
 81 M E L S S L R S E D T A V Y Y C A R R G
241 ATGGAGCTGAGCAGCCTGAGATCTGAGGACACAGCCGTGTATTACTGTGCAAGACGGGGG
101 E Y G N Y E G A M D Y W G Q G T L V T V
301 GAGTATGGTAACTACGAGGGGGCTATGGACTACTGGGGCCAGGGAACCCTGGTCACCGTC
121 S S           (SEQ ID NO: 42)
361 TCCTCA        (SEQ ID NO: 58)
```

Hu-G1-VH_v2_nuc-B

```
  1 Q V Q L V Q S G A E V K K P G A S V K V
  1 CAGGTGCAGCTGGTACAGTCAGGAGCTGAAGTGAAGAAGCCTGGGGCTTCAGTGAAGGTC
 21 S C K V S G Y T F T S Y D I N W V R Q A
 61 TCCTGCAAGGTTTCTGGTTACACCTTCACAAGCTACGATATAAATTGGGTGCGACAGGCT
 41 P G K G L E W I G W I Y P G D G S I K Y
121 CCTGGAAAAGGACTTGAGTGGATTGGATGGATTTATCCTGGAGATGGTAGCATTAAGTAC
 61 N E K F K G K A T L T V D K S T D T A Y
181 AATGAGAAATTCAAGGGCAAGGCCACACTGACTGTAGACAAATCCACAGACACAGCCTAC
 81 M E L S S L R S E D T A V Y Y C A R R G
241 ATGGAGCTGAGCAGCCTGAGATCTGAGGACACAGCAGTCTATTACTGTGCAAGACGGGGG
101 E Y G N Y E G A M D Y W G Q G T L V T V
301 GAGTATGGTAACTACGAGGGGGCTATGGACTACTGGGGCCAAGGGACCCTGGTCACCGTC
121 S S           (SEQ ID NO: 43)
361 TCCTCA        (SEQ ID NO: 59)
```

CDR amino acids are indicated in italics and in bold; mouse framework substitutions are marked in bold and underlined. The codons identified in bold alone indicate codons that were switched to less rare ones.

Example 4

Determination of the Binding Affinity and Specificity of a Humanized G1 Anti-P-Selectin Antibody Method All experiments were performed on a Biacore 3000, at 25° C., using 20 mM MOPS, pH 7.5, 150 mM NaCl, 1.5 mM $CaCl_2$ and 0.005% Tween-20 as running buffer. Low densities of soluble P-selectin or soluble E-selectin (control protein) were covalently coupled on two different surfaces of a CM-5 chip according to the manufacturer's instructions. The coating density was selected with the aim of achieving a maximum binding response of 100-200 RUs.

Figure 4:
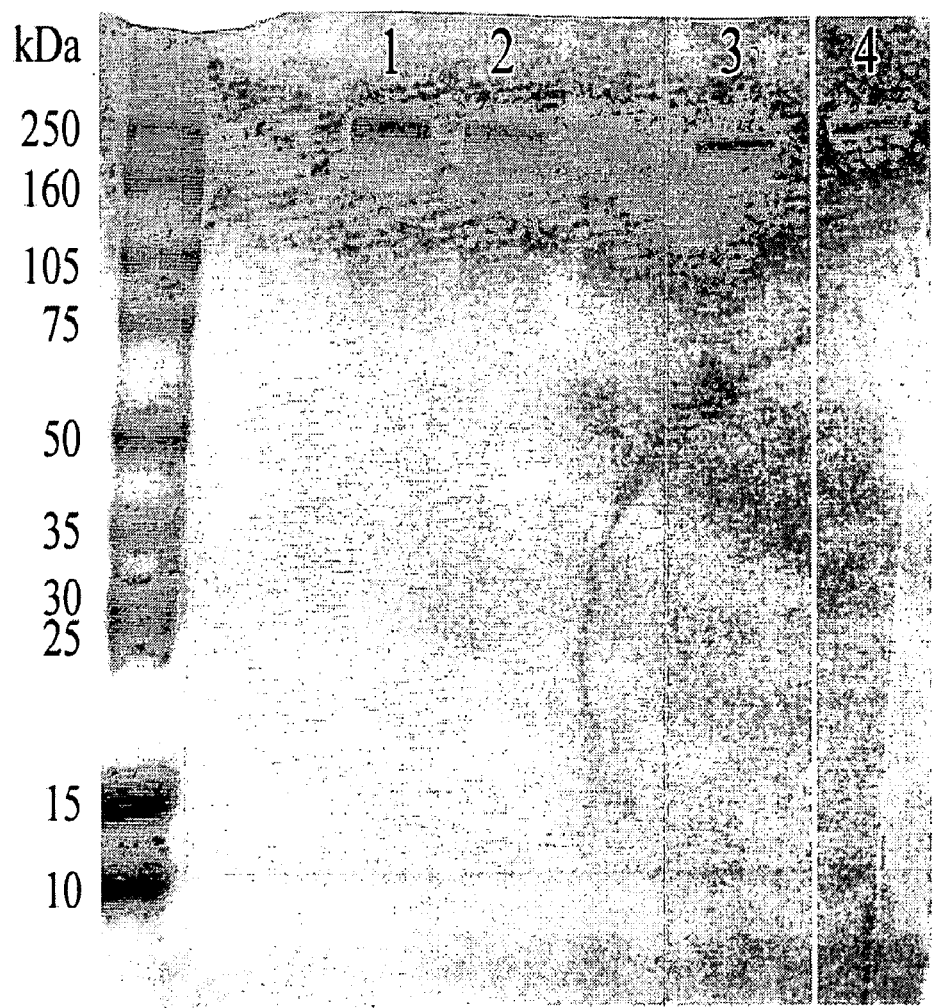
FIG. 4 is a photograph showing the results following expression of a humanized G1 antibody ($G1_{aggr}$) in stable CHO dhfr⁻ cells and purification of the $G1_{aggr}$ antibody using one step purification on a protein A column. The photograph shows the purified $G1_{aggr}$ antibody (lane 3) in comparison with the G1 mouse parental monoclonal antibody from which it was derived (lane 4). Lane 1 shows 1.0 µg of human IgG. Lane 2 shows 0.5 µg of human IgG.

A humanized G1 antibody design labeled "aggressive" ($G1_{aggr}$) was expressed in stable CHO dhfr⁻ cells grown to exhaustion and the media harvested. This design refers to humanized antibody VL sequence "Hu-G1-VK_v1" (SEQ ID NO: 46) and VH sequence "Hu-G1-VH_v1" (SEQ ID NO: 50). The antibody was subjected to one step purification on a protein A column, eluted with 0.1M glycine pH 2.8, immediately neutralized by addition of 0.5M $NaPO_4$, and the yield and concentration determined by A280 protein determination. An aliquot of each antibody (the humanized antibody $G1_{aggr}$, a G1 mouse parental monoclonal antibody, and two concentrations (1.0 μg and 0.5 μg of human IgG) was run on a 4-20% gradient non-reducing SDS-PAGE and stained with coomassie blue. The humanized antibody $G1_{aggr}$ was compared with the G1 mouse parental monoclonal antibody from which it was derived. The gel (FIG. 4) shows there was no contamination or breakdown products for the antibodies and all ran as dimers of approximately the same apparent molecular weight.

Solutions containing $G1_{aggr}$ and the G1 mouse parental monoclonal antibody were diluted and injected onto the CM-5 chip at a flow rate of 30 μl/min for 4 minutes, followed by 3 min to allow for dissociation, at which time the bound antibody was eluted with a 10 μl injection of 10 mM Acetate pH 4.5, 100 mM NaCl at a flow rate of 10 μl/min. A series of concentrations of both antibodies were injected over the soluble P-selectin and the soluble E-selectin surfaces until saturating binding was observed.

Figure 5:
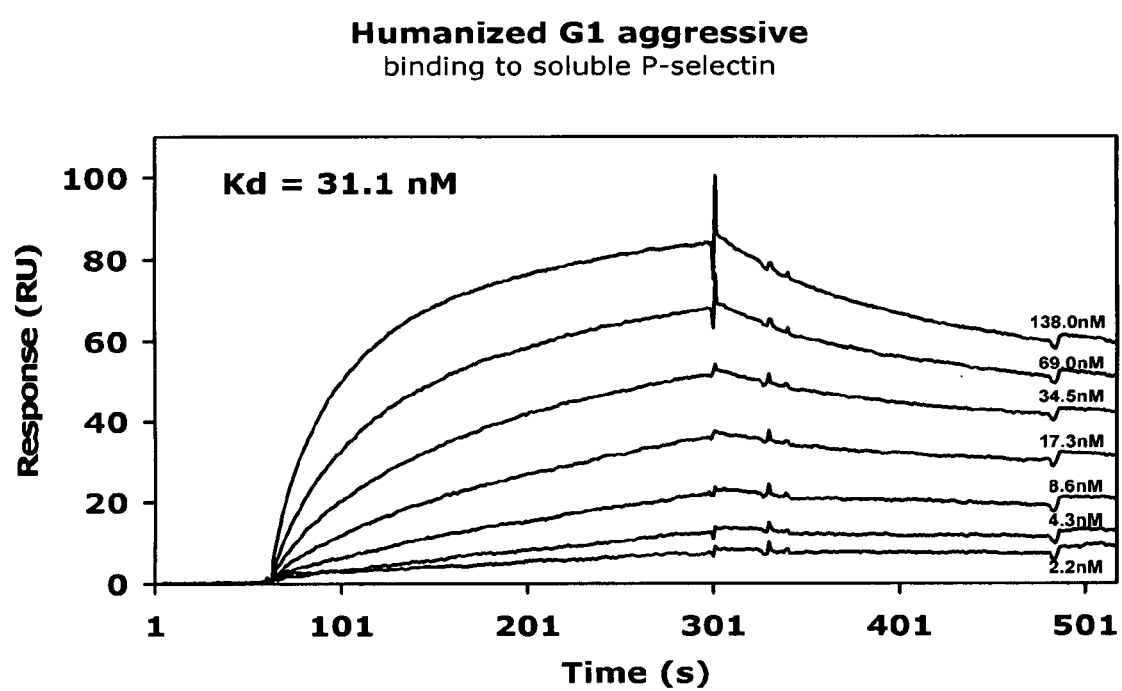
FIG. 5 is a graph showing the equilibrium affinity of the indicated concentrations of humanized antibody $G1_{aggr}$ for soluble p-selectin.

The data were analyzed using the Biaevaluation software v 4.1. Sensorgrams from the different cycles were overlaid and the data for all curves of one antibody were simultaneously fitted to a Bivalent analyte model (see FIG. 5). The equilibrium affinity was calculated from the on-rates and off-rates obtained from this analysis.

Based on these analyses, the apparent $K_d$ for the humanized $G1_{aggr}$ was calculated to be 31.1 nM. This compared favorably to a calculated $K_d$ for the parental G1 murine antibody of 24.4 nM. There was no binding observed for either antibody to E-selectin. These results indicate that the humanized $G1_{aggr}$ antibody exhibits specificity for P-selectin and can be used as a P-selectin antagonist.

Other Embodiments

All publications and patent applications, including U.S. Ser. No. 60/872,170, mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

What is claimed is:

1. A humanized antibody, or binding fragment thereof, comprising an immunoglobulin light chain variable region comprising SEQ ID NO:36, and an immunoglobulin heavy chain variable region comprising SEQ ID NO:40, and wherein the humanized antibody has binding specificity for P-selectin.

2. The humanized antibody of claim 1, wherein said antibody binds P-selectin with a dissociation constant less than $10^{-7}$ M.

3. The humanized antibody of claim 1, wherein said antibody binds P-selectin with a dissociation constant between $10^{-7}$ M and $10^{-13}$ M.

4. The humanized antibody of claim 1, wherein said humanized antibody is recombinant.

5. The humanized antibody of claim 1, wherein said antibody is an immunoglobulin G.

6. A pharmaceutical composition comprising the antibody of claim 1 admixed with a pharmaceutically acceptable excipient.

7. A kit comprising the pharmaceutical composition of claim 6 and instructions.

* * * * *

UNITED STATES PATENT AND TRADEMARK OFFICE

(12)      CERTIFICATE EXTENDING PATENT TERM
UNDER 35 U.S.C. § 156

| | | | |
|---|---|---|---|
| (68) | PATENT NO. | : | 8,377,440 |
| (45) | ISSUED | : | February 19, 2013 |
| (75) | INVENTOR | : | McEver et al. |
| (73) | PATENT OWNER | : | Novartis AG; and Oklahoma Medical Research Foundation |
| (95) | PRODUCT | : | ADAKVEO® (crizanlizumab-tmca) |

This is to certify that an application under 35 U.S.C. § 156 has been filed in the United States Patent and Trademark Office, requesting extension of the term of U.S. Patent No. 8,377,440 based upon the regulatory review of the product ADAKVEO® (crizanlizumab-tmca) by the Food and Drug Administration. According to United States Patent and Trademark Office records, the original expiration date of the patent as of the date of issuance of this certificate is April 28, 2028. Because it appears that the requirements of the law have been met, this certificate extends the term of the patent for the period of

(94)                                  1,323 days subject to the payment of maintenance fees as provided by law, with all rights pertaining thereto as provided by 35 U.S.C. § 156.

I have caused the seal of the United States Patent and Trademark Office to be affixed this 22nd day of May 2023.

Kathi Vidal

Katherine K. Vidal
Under Secretary of Commerce for Intellectual Property and Director of the United States Patent and Trademark Office